(12) United States Patent
Llano-Sotelo et al.

(10) Patent No.: US 8,648,035 B2
(45) Date of Patent: Feb. 11, 2014

(54) IDENTIFICATION AND USE OF PEPTIDE INHIBITORS OF PROTEIN SYNTHESIS

(75) Inventors: Beatriz Llano-Sotelo, Prospect Heights, IL (US); Alexander S. Mankin, River Forest, IL (US); Dorota Klepacki, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 231 days.

(21) Appl. No.: 12/673,283

(22) PCT Filed: Aug. 18, 2008

(86) PCT No.: PCT/US2008/073468
§ 371 (c)(1),
(2), (4) Date: Feb. 25, 2011

(87) PCT Pub. No.: WO2009/026218
PCT Pub. Date: Feb. 26, 2009

(65) Prior Publication Data
US 2011/0143998 A1  Jun. 16, 2011

Related U.S. Application Data

(60) Provisional application No. 60/956,650, filed on Aug. 17, 2007.

(51) Int. Cl.
*A61K 35/00* (2006.01)
(52) U.S. Cl.
USPC .............. 514/2.4; 514/1.1; 530/300; 530/329
(58) Field of Classification Search
USPC .......................................................... 514/2.4
See application file for complete search history.

(56) References Cited

U.S. PATENT DOCUMENTS

| 4,683,195 A | 7/1987 | Mullis et al. | |
|---|---|---|---|
| 2003/0153002 A1* | 8/2003 | Steitz et al. | 435/7.1 |
| 2007/0197444 A1* | 8/2007 | Herman et al. | 514/13 |

FOREIGN PATENT DOCUMENTS

WO   WO 2006/122277   * 11/2006 ............... C12Q 1/68

OTHER PUBLICATIONS

Pierce et al., "The Complete Genome Sequence of Moorella thermoacetica", Environ. Microbiol. (2008) 10, 2550-2573.*
Garnett, W.R., Clin. Pharm. 1:307-314 (1982) abstract.
Brogden, R.N. et al., Drugs 27:194-209 (1984) abstract.
McCarthy, D.M., New Eng J Med., 325:1017-1025 (1991).
Molecular Cloning A Laboratory Manual, 2nd Ed., ed. by Sambrook, J. et al. (Cold Spring Harbor Laboratory Press (1989) Table of contents.
Short Protocols in Molecular Biology, 3rd Ed., ed. by Ausubel, F. et al. (Wiley, NY (1995) Table of contents.
DNA Cloning, vols. I and II (D. N. Glover ed., 1985); Oligonucleotide Synthesis (M. J. Gait ed. (1984) Table of contents.
Nucleic Acid Hybridization (B. D. Hames & S. J. Higgins eds. (1984) Table of contents.
Immunochemical Methods in Cell and Molecular Biology (Mayer and Walker, eds., Academic Press, London (1987) Table of contents.
Handbook of Experimental Immunology, vols. I-IV (D. M. Weir and C. C. Blackwell, eds. (1986) Table of contents.
Miller, J. Experiments in Molecular Genetics (Cold Spring Harbor Press, Cold Spring Harbor, N.Y. (1972) Table of contents.
Gait, M.J. ed., Oligonucleotide Synthesis (1984).
Gu, Y. et al., World Journal of Gastroenterology, vol. 10, No. 11, pp. 1583-1588, 2004.
Pustowka, A. et al., ChemBioChem, vol. 4, pp. 1093-1097, 2003.
International Preliminary Report on Patentability dated Mar. 4, 2010 for International Application No. PCT/US2008/073468.

* cited by examiner

*Primary Examiner* — Karlheinz R Skowronek
*Assistant Examiner* — Catherine Mader
(74) *Attorney, Agent, or Firm* — Nutter McClennen & Fish LLP; Konstantin M. Linnik

(57) ABSTRACT

The present invention discloses compositions of peptide inhibitors of protein synthesis, and methods of identifying peptide inhibitors that are capable of inhibiting protein synthesis through an interaction at a stem-loop H18 in 16S rRNA of a 30S ribosomal subunit. Screening methods for peptides are disclosed, in addition to methods of determining the affinity of a test compound for a ribosomal subunit.

10 Claims, 7 Drawing Sheets

SEQUENCE LISTING

<160> NUMBER OF SEQ ID NOS: 33

<210> SEQ ID NO 1
<211> LENGTH: 49
<212> TYPE: RNA
<213> ORGANISM: Bacillus anthracis

<400> SEQUENCE: 1
ggggccacgg cuaacuacgu gccagcagcc gcgguaauac guaggguggc        49

<210> SEQ ID NO 2
<211> LENGTH: 7
<212> TYPE: PRT
<213> ORGANISM: Artificial Sequence
<220> FEATURE:
<223> OTHER INFORMATION: Synthetic construct

<400> SEQUENCE: 2

Ala Gly Ala Ala Met Ser His
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic construct

<400> SEQUENCE: 3

Ala Met Ser Ala Pro Ile Pro
1               5

<210> SEQ ID NO 4
<211> LENGTH: 7

```
<212> TYPE: PRT
<213> ORGANISM: Artificial Sequence
<220> FEATURE:
<223> OTHER INFORMATION: Synthetic construct

<400> SEQUENCE: 4

Ser Ile Leu Pro Tyr Pro Tyr
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic construct

<400> SEQUENCE: 5

Val Gln Ser Leu Pro Ser Pro
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 6

Ser Xaa Pro Xaa Pro
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(3)
<223> OTHER INFORMATION: Xaa can be any naturally occurring amino acid

<400> SEQUENCE: 7

Ser Xaa Xaa Leu Pro Thr
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic construct

<400> SEQUENCE: 8

Leu Ser Pro Lys Leu Pro Thr
1               5

<210> SEQ ID NO 9
<211> LENGTH: 7
<212> TYPE: PRT
<213> ORGANISM: Artificial Sequence
<220> FEATURE:
```

<223> OTHER INFORMATION: Synthetic construct

<400> SEQUENCE: 9

Ser Ser Leu Leu Pro Thr Thr
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic construct

<400> SEQUENCE: 10

Phe Pro Gly His Ser Gly Pro
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic construct

<400> SEQUENCE: 11

Glu Pro Leu Gln Leu Lys Met
1               5

<210> SEQ ID NO 12
<211> LENGTH: 7
<212> TYPE: PRT
<213> ORGANISM: Artificial Sequence
<220> FEATURE:
<223> OTHER INFORMATION: Synthetic construct

<400> SEQUENCE: 12

Thr Pro His Asn Thr Ser Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic construct

<400> SEQUENCE: 13

Gln Trp Thr Trp Thr Gln Tyr
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic construct

<400> SEQUENCE: 14

Leu Thr His Pro Arg Trp Pro
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic construct

```
<400> SEQUENCE: 15

Thr Lys Thr Asp Thr Trp Leu
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic construct

<400> SEQUENCE: 16

Asn Thr Pro Gln Gly Met Thr
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic construct

<400> SEQUENCE: 17

Thr His Pro Leu Leu Leu Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic construct

<400> SEQUENCE: 18

Gly His Trp Glu Ala Arg Glu
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic construct

<400> SEQUENCE: 19

Ala Val Pro Arg Ala Ser Phe
1               5

<210> SEQ ID NO 20
<211> LENGTH: 7
<212> TYPE: PRT
<213> ORGANISM: Artificial Sequence
<220> FEATURE:
<223> OTHER INFORMATION: Synthetic construct

<400> SEQUENCE: 20

Tyr His Pro Met Pro Val Pro
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic construct

<400> SEQUENCE: 21
```

```
Thr Pro Thr Thr Asp Gly Pro
1               5

<210> SEQ ID NO 22
<211> LENGTH: 7
<212> TYPE: PRT
<213> ORGANISM: Artificial Sequence
<220> FEATURE:
<223> OTHER INFORMATION: Synthetic construct

<400> SEQUENCE: 22

Val His Arg His Pro Pro His
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic construct

<400> SEQUENCE: 23

Thr His Pro Leu Leu Leu Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic construct

<400> SEQUENCE: 24

Gly His Trp Glu Ala Arg Glu
1               5

<210> SEQ ID NO 25
<211> LENGTH: 7
<212> TYPE: PRT
<213> ORGANISM: Artificial Sequence
<220> FEATURE:
<223> OTHER INFORMATION: Synthetic construct

<400> SEQUENCE: 25

Thr Lys Thr Asp Thr Trp Leu
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic construct

<400> SEQUENCE: 26

Thr Pro Thr Thr Asp Gly Pro
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic construct

<400> SEQUENCE: 27

Met Lys His Pro Pro Arg Ile
1               5
```

```
<210> SEQ ID NO 28
<211> LENGTH: 7
<212> TYPE: PRT
<213> ORGANISM: Artificial Sequence
<220> FEATURE:
<223> OTHER INFORMATION: Synthetic construct

<400> SEQUENCE: 28

Gly Thr Met Leu Ala Ala Val
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic construct

<400> SEQUENCE: 29

Thr Met Thr Pro Pro Thr Arg
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic construct

<400> SEQUENCE: 30

Gly Asn Asp Trp Pro His Trp
1               5

<210> SEQ ID NO 31
<211> LENGTH: 7
<212> TYPE: PRT
<213> ORGANISM: Artificial Sequence
<220> FEATURE:
<223> OTHER INFORMATION: Synthetic construct

<400> SEQUENCE: 31

Glu His Pro Tyr Ile Thr Val
1               5

<210> SEQ ID NO 32
<211> LENGTH: 7
<212> TYPE: PRT
<213> ORGANISM: Artificial Sequence
<220> FEATURE:
<223> OTHER INFORMATION: Synthetic construct

<400> SEQUENCE: 32

Asn Thr Asn Thr Leu His Leu
1               5

<210> SEQ ID NO 33
<211> LENGTH: 7
<212> TYPE: PRT
<213> ORGANISM: Artificial Sequence
<220> FEATURE:
<223> OTHER INFORMATION: Synthetic construct

<400> SEQUENCE: 33

Ser Tyr Pro Asp Leu His Leu
1               5
```

IDENTIFICATION AND USE OF PEPTIDE INHIBITORS OF PROTEIN SYNTHESIS

GOVERNMENT SUPPORT

The invention was supported by National Institutes of Health Grant No.: U19 AI56575. The government has certain rights in the invention.

FIELD OF THE INVENTION

The present invention concerns the identification and use of novel peptide inhibitors of protein synthesis. Specifically, screening methods for peptides that interfere with protein synthesis by binding to a ribosomal subunit are disclosed.

BACKGROUND OF THE INVENTION

According to the U.S. Centers for Disease Control and Prevention over 40,000 people in North America die each year from infections caused by drug-resistant germs. Emerging bacterial resistance to currently known classes of antibiotics is a major worldwide health problem. In addition, the most commonly used antibiotics (e.g., macrolides, beta-lactams, and quinolones) were initially introduced more than thirty years ago. Antibiotic resistance is a critical health problem, aggravated by the emergence of multidrug-resistant bacteria, and requires urgent attention by the scientific community.

The overuse of antibiotics have sped up evolutionary adaptations that enable bacteria and other microbes, such as viruses, fungi, and parasites, to survive these drugs. In addition, recent studies have shown that the common use of antibacterial products, such as soaps, hand santizers, and household, can lead to the development of tolerance for certain antibiotics. For example, such "cross-resistance" has been shown between triclosan, a common chemical in antibacterial hand sanitizer, and drug resistance to isoniazid, an antibiotic used for treating tuberculosis.

Drug resistance is an increasingly difficult problem in hospitals since critically ill patients are less able to fight off infections without the help of antibiotics. Heavy use of antibiotics in these patients selects for drug resistance strains of bacteria. Unfortunately, this worsens the problem by producing bacteria with greater ability to survive in the presence of even the strongest antibiotics. These "superbugs" have even developed resistance to vancomycin, which was once considered the "antibiotic of last resort".

A key factor in the development of antibiotic resistance is the ability of infectious organisms to adapt quickly to new environmental conditions. Bacteria are single-celled organisms with a relatively small numbers of genes and can reproduce rapidly. Therefore, a mutation that helps a microbe survive exposure to an antibiotic will quickly become dominant throughout the microbial population. The increasing pace with which bacteria evolve drug resistance coupled with the lack of new classes of antibiotics has driven the need for new research strategies.

Accordingly, there exists a need for new antibiotic targets, and methods of identifying new antibiotics. In particular, new compositions capable of inhibiting protein synthesis and/or new antibacterials targeting new sites in the ribosome would satisfy a long-felt therapeutic need.

SUMMARY OF THE INVENTION

In one aspect, the invention provides methods for selecting a peptide having a desired affinity for a target nucleic acid sequence. The method comprises the steps of presenting a target nucleic acid sequence as an extended target molecule having an enzymatically cleavable moiety and an affinity linker joined to the target sequence; exposing the tagged target molecule to a phage display library that provides a plurality of peptides such that a peptide/target molecule complex is formed if a binding peptide with an affinity for the target nucleic acid sequence is present in the library; isolating the peptide/target molecule complex by binding the affinity linker component of the complex with a binding partner; and enzymatically cleaving the peptide and target nucleic acid sequence from the bound complex. The binding peptide can then be isolated or identified from the cleaved portion of the complex. In some embodiments, the method further comprises tagging the extended target molecule with an affinity linker. The method can further include washing at each step.

In some embodiments, the extended target molecule can be an RNA/organic molecule construct, or an RNA/DNA construct. The target nucleic acid sequence can be a ribosomal subunit sequence. For example the target nucleic acid sequence can be a mimetic of a stem-loop H18 in 16S rRNA of a 30S ribosomal subunit. In some embodiments, the extended target molecule can be an RNA/DNA construct with substantially similar three dimensional structure to a stem-loop H18 in 16S rRNA of a 30S ribosomal subunit. In a preferred embodiment, the enzymatically cleavable moiety can be DNA. The step of enzymatically cleaving the binding target compound can comprise using DNase I.

The combination of the affinity linker and the binding partner can be selected from the group consisting of: biotin-avidin and/or streptavidin, lectin-saccharide, protein A and/or protein G-immunoglobulin constant region, Tag peptide sequence-Tag antibody, an hapten-antibody, a receptor-ligand, and Ni-NTA. In some embodiments, the binding partner is immobilized, such as, but not limited to, immobilized onto a solid support, such as a bead, a surface, column, a magnetic bead, a magnetized particle, or a microtiter plate. For example, the RNA/DNA hybrid-ligand can bind specifically to the phage on one site, and to a solid support (e.g., beads or wells) on the ligand site. The release of the captured phage-RNA/DNA complex from the solid support can be done using enzymatic digestion.

In some embodiments, the identified test compound can be an antimicrobial compound which interacts with a ribosomal subunit so as to inhibit protein synthesis.

In another aspect, the invention provides compositions comprising a peptide selected from Table 1 and Table 2 and analogs and derivatives thereof, wherein the peptide is capable of inhibiting protein synthesis. The composition can further include a pharmaceutically acceptable carrier. The peptide is capable of binding to a stem-loop H18 in 16S rRNA. In some embodiments, the peptide is coupled to a moiety capable of directing the peptide to a target cell. In other embodiments, the composition further comprises a combination of the identified peptides and one or more drug. For example, in some embodiments, one or more antimicrobial or antibacterial can be combined with the peptides. In preferred embodiments, the drugs have a synergistic effect.

In another aspect, the invention discloses an isolated therapeutic peptide composition comprising a sequence of at least seven amino acids capable of inhibiting protein synthesis through an interaction at a stem-loop H18 in 16S rRNA of a 30S ribosomal subunit. In some embodiments, the peptide exhibits at least about 25 percent inhibition of protein synthesis in a cell-free translational assay, or at least about 30 percent, or preferably at least about 50 percent, or preferably at least about 60 percent, or preferably at least about 70 percent, or more preferably at least about 80 percent inhibition of protein synthesis in a cell-free translational assay. The peptide is in the range of about seven to about thirty amino acid residues and selectively binds to the stem-loop H18 in 16S rRNA of the 30S ribosomal subunit. In some embodiments, the peptide is in the range of about seven to about twenty amino acid residues, or in the range of about five to about twelve amino acid residues. The peptide sequence can include at least one sequence selected from the group consisting of SEQ ID NOS: 2-33. In some embodiments, the peptide sequence includes at least one of the amino acid motifs selected from the group consisting of AMS, HPP, THP, LHL, SXPXP (SEQ ID NO: 6) and SXXLPT (SEQ ID NO: 7). Preferred peptide sequence include, for example, SEQ ID NO: 2, SEQ ID NO: 3, and SEQ ID NO: 28. In some embodiments, the therapeutic peptide composition further includes a pharmaceutically acceptable carrier. In other embodiments, the peptide can be coupled to a moiety capable of directing the peptide to a target cell.

In some embodiments, the invention discloses isolated therapeutic peptides consisting of a sequence of no more than 30 amino acid residues, said sequence of amino acid residues including at least one sequence selected from Tables 1 and 2 (SEQ ID Nos: 2-33). In some embodiments, the therapeutic peptides have between about 7 amino acid residues to about 30 amino acid residues, or preferably between about 7 amino acid residues to about 20 amino acid residues, or more preferably between about 7 amino acid residues to about 12 amino acid residues. In preferred embodiments, the invention discloses isolated therapeutic peptides consisting of a sequence of no more than 30 amino acid residues, said sequence of amino acid residues including the three amino acid motif AMS. In other embodiments, the invention discloses isolated therapeutic peptides consisting of a sequence of no more than 30 amino acid residues, said sequence of amino acid residues including at least one of the amino acid motifs selected from the group consisting of AMS, HPP, THP, LHL, SXPXP (SEQ ID NO: 6) and SXXLPT (SEQ ID NO: 7). In other embodiments, the invention discloses isolated therapeutic peptides consisting of a sequence of no more than 30 amino acid residues, said sequence of amino acid residues including at least one of SEQ ID NOS: 2-33, preferably at least one of SEQ ID NO: 2, SEQ ID NO: 3, and SEQ ID NO: 28.

In another aspect, the invention provides a method for treating a bacterial infection in a subject comprising administrating a peptide capable of inhibiting protein synthesis through an interaction at a stem-loop H18 in 16S rRNA of a 30S ribosomal subunit. The peptide can, for example, be selected from Tables 1 and 2, or derivatives or isotopes thereof, or other peptides identified using the method of the present invention. The peptide can be delivered in an amount sufficient to inhibit the growth of bacteria in vivo. Non-limiting examples of a bacteria include, for example, Gram-positive bacteria such as *Bacillus anthracis, Actinomyces bovis, Enterococcus fetalis, Hemophilus pneumoniae, Listeria monocytogenes, Mycobacterium tuberculosis, M. leprae, M smegmatis, Proprionibacterium acnes, Sarcina ventriculi, Staphylococcus aureus, S. epidermis, S. intermedias, Streptococcus hemolyticus, & pneumoniae*; Gram-negative bacteria such as *Campylobacter fetus, Erwinia carotovora, Flavobacterium meningosepticum, Helicobacter pylori, Hemophilus pneumoniae, H. influenzae, Klebsiella pneumonia, Neisseria gonorrhoeae, Pseudomonas aeruginosa, Shigella dysenteria, Salmonella typhi, S. paratyphi, Yersinia pestis, Escherichia coli* serotype 0157, and *Chlamydia* species, *Helicobacter* species. In some embodiments, the peptide is delivered locally or regionally to a site of infection. The peptide can administered to a wound site, applied topically, delivered systemically, delivered via intravenous or intraarterial injection. The method can further include administering to the subject one or more antimicrobial compounds.

In another aspect, the invention provides a method for preventing a microbial infection in a subject comprising administrating a peptide capable of inhibiting protein synthesis through an interaction at a stem-loop H18 in 16S rRNA of a 30S ribosomal subunit in an amount sufficient to inhibit the growth of microbes in vivo.

In another aspect, the invention method for preventing microbial growth in a solution comprising mixing said solution with a peptide capable of inhibiting protein synthesis through an interaction at a stem-loop H18 in 16S rRNA of a 30S ribosomal subunit in an amount sufficient to inhibit the microbial growth in said solution.

In another aspect, the invention provides a method for preventing bacterial attachment or growth on an abiotic surface comprising coating said surface with a peptide capable of inhibiting protein synthesis through an interaction at a stem-loop H18 in 16S rRNA of a 30S ribosomal subunit in an amount sufficient to inhibit the growth of bacteria on said abiotic surface. The surface is part of a medical device. Non-limiting examples of a medical device include a syringe, a stent, a catheter, fluid container, a pacemaker, and an implantable pump.

In another aspect, the invention provides peptides comprising consensus sequence AMS capable of inhibiting protein synthesis. The peptide is capable of binding to 30S ribosomal subunit. The binding can involve an interaction with the stem-loop H18 in 16S rRNA.

In another aspect, the invention discloses peptide selected from Table 1 and Table 2 (SEQ ID Nos: 2-33) and analogs and derivatives thereof. The peptides can be used to inhibit protein synthesis in prokaryotes, and/or eukaryotes. In some embodiments, the peptides can be attached to a molecule to direct the peptide to a target cell. In other embodiments, the peptide sequences can be used in screening assays and/or ligand-displacement assays. For example, the peptides can be fluorescently, radioactively, and/or luminescently labeled. The peptide sequences can be coupled to organic groups, fluorescent molecules, radioactive isotopes, other antibiotics, crosslinking agents, and/or oligonucleotides. In yet another embodiment, the peptides can be used as surrogate ligands for high-throughput screening. In some embodiments, the peptides can be used as antimicrobial or antibacterial agents. In other embodiments, the peptides can be used as anticancer agents. In other embodiments, the peptides of the present invention can be used as peptidomimetic drugs. In other embodiments, the peptides can be used as lead compounds to construct libraries of derivatives based on their sequence. The libraries of derivatives can be used in computational docking studies. In other embodiments, the peptides can be used as lead compounds in structure-based virtual screening of libraries. In yet another embodiment, the peptides can be used as surrogate ligands for high-throughput screening.

In another aspect, the invention provides methods of determining the affinity of a test compound for a ribosomal subunit comprising the steps of incubating a ribosomal subunit with one or more detectably labeled peptides of Tables 1 and 2 (SEQ ID Nos: 2-33); detecting the labeled peptide bound to the ribosomal subunit; contacting a test compound with the ribosomal subunit in the presence of the one or more labeled peptides of Tables 1 and 2; and determining binding of the test compound to said ribosomal subunit by measuring the change in the detectable label. In yet another aspect, the invention provides a method of identifying test compounds with binding affinity to a ribosomal subunit, comprising contacting a ribosomal subunit with a detectably labeled peptide of the present invention to form a labeled complex and measuring a signal from said labeled complex to determine a baseline signal; incubating a ribosomal subunit with a test compound to form a mixture; adding the detectably labeled peptide to said mixture of the ribosomal subunit and the test compound; measuring the signal from said mixture; comparing the baseline signal with the signal from the mixture, whereby a modulation in said signal indicates that the test compound binds to the ribosomal subunit. The detectable label can be selected from the list consisting of a fluorescent label, a chemiluminescent label, a colorimetric label, an enzymatic marker, and a radioactive isotope. For example, the fluorescent label can be selected from the non-limiting list consisting of dansyl, fluorescein, Oregon green, rhodamine, tetra-methyl rhodamine, Texas-red, phycoerythrin, BODIPY fluorophore, and $Eu^{3+}$. The methods can determine affinity for the stem-loop H18 in 16S rRNA of a 30S ribosomal subunit.

DETAILED DESCRIPTION OF THE INVENTION

Figure 1:
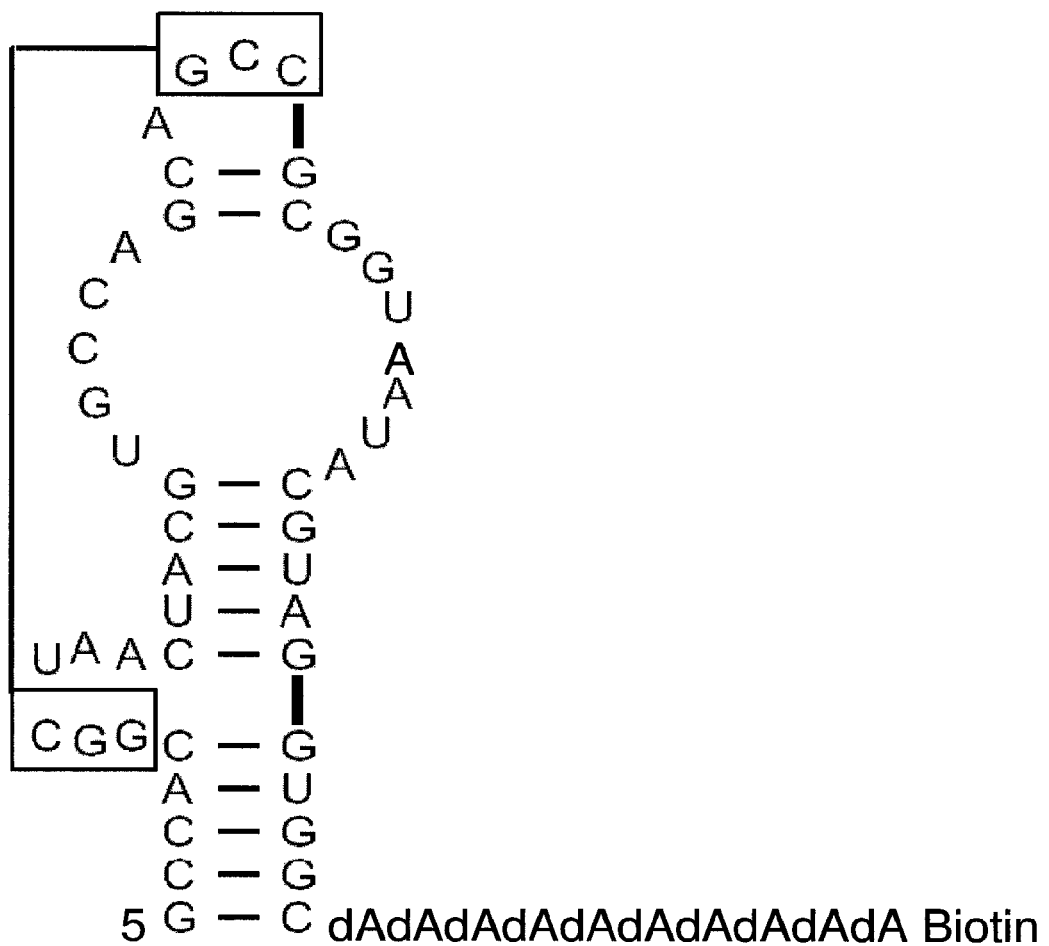
FIG. 1 is schematic of the RNA sequence (SEQ ID NO. 1) and secondary structure of the stem-loop H18 RNA/DNA hybrid from the 16S rRNA of *B. anthracis*.

The terms used in this invention are, in general, expected to adhere to standard definitions generally accepted by those having ordinary skill in the art of microbiology. A few exceptions, as listed below, have been further defined within the scope of the present invention.

The term "antimicrobial compound" as used herein, refers to any compound that reduces microbial growth. Such a compound includes, but is not limited to, polypeptides, proteins, small molecular weight organic molecules, hormones, and the like. The term "antimicrobial compound" is art-recognized and is intended to include a compound which inhibits the proliferation or viability of a microbe which is undesirable and/or which disrupts a microbial cell. The language further includes significant diminishment of a biological activity which is undesirable and associated with the microbe, such that a subject would not be detrimentally affected by the microbe. Examples include antibiotics, biocides, antibacterial compounds.

The term "test compound" as used herein, refers to any compound suspected of having a capability of interacting with a ribosomal subunit that results in antimicrobial activity. For example, a "test compound" includes, but is not limited to, protein translation inhibitors, peptides, metabolic inhibitors, polypeptides, small molecular weight organic molecules, and the like. The term "compound" is art-recognized and includes compounds being tested for antimicrobial activity. The compound can be designed to incorporate a moiety known to interact with a ribosomal subunit or can be selected from a library of diverse compounds, e.g., based on a desired activity, e.g., random drug screening based on a desired activity. Preferably, the compound of the present invention is a small molecule. Examples of compounds of the present invention include peptides listed in Tables 1 and 2.

The term "ribosomal protein" as used herein, refers to any polypeptide that is assembled into a functional ribosome. For example, a bacterial ribosomal protein includes, but is not limited to, S12, L16, L35, or L36.

The term "ribosomal nucleic acid" as used herein, refers to any nucleic acid that is assembled into a functional ribosome. For example, a bacterial nucleic acid includes, but is not limited to, 5S, 16S, 23S, 30S, 50S rRNA.

The term "peptide" as used herein, refers to a condensed polymer of amino acids within which each amino acid is joined by a peptide bond to the immediately preceding and to the immediately subsequent amino acid in the chain. A peptide comprises a first amino acid, generally referred to as the amino-terminal amino acid, and a last amino acid, generally referred to as the carboxyl terminal amino acid. Peptides include, but are not limited to, linear, branched, or cyclic forms. Generally, a peptide comprises a mixture of less than 50, less than 40, less than 30, preferably less than 20, most preferably less than 15 naturally occurring or synthetic amino acids. The amino acid may be covalently modified.

The term "protein translation" as used herein, refers to the process whereby free amino acids are enzymatically condensed into peptidergic polymers, thus forming polypeptides and proteins. The formation of peptide bonds is facilitated by intracellular structures (ribosomes) that provide support and enzymatic control for the polymer synthesis.

The term "small molecular weight organic molecule" refers to any protease-resistant compound capable of interacting with a polypeptide or protein. For example, a small molecular weight organic molecule may range between approximately 5-1,500 daltons, preferably between 100-750 daltons, and more preferably between 250-500 daltons.

The term "infectious disease" is meant to include disorders caused by one or more species of bacteria, viruses, fungi, and protozoans, species of which that are disease-producing organisms collectively referred to as "pathogens." The term "fungi" is meant to include the yeasts. In this invention, pathogens are exemplified, but not limited to, Gram-positive bacteria such as *Actinomyces bovis, Enterococcus fecalis, Hemophilus pneumoniae, Listeria monocytogenes, Mycobacterium tuberculosis, M. leprae, M smegmatis, Proprionibacterium acnes, Sarcina ventriculi, Staphylococcus aureus, S. epidermis, S. intermedias, Streptococcus hemolyticus, & pneumoniae*; Gram-negative bacteria such as *Campylobacter fetus, Erwinia carotovora, Flavobacterium meningosepticum, Helicobacter pylori, Hemophilus pneumoniae, H. influenzae, Klebsiella pneumonia, Neisseria gonorrhoeae, Pseudomonas aeruginosa, Shigella dysenteria, Salmonella typhi, S. paratyphi, Yersinia pestis, Escherichia coli* serotype 0157, and *Chlamydia* species, *Helicobacter* species; viruses such as HIV-1, -2, and -3, HSV-I and -II, non-A non-B non-C hepatitis virus, pox viruses, rabies viruses, and Newcastle disease virus; fungi such as *Candida albicans, C. tropicalis, C. krusei, C. pseudotropicalis, C. parapsilosis, C. quillermondii, C. stellatoidea, Aspergillus fumigatus, A. niger, A. nidulans, A. flavus, A. terreus, Absidia corymbifera, A. ramosa, Cryptococcus neoforms, Histoplasma capsulatum, Coccidioides immitis, Pneumocystis carinii, Rhizopus arrhizus, R. oryzae, Mucor pusillus* and other fungi; and protozoa such as *Entamoeba histolytica, Entamoeba coli, Giardia lamblia, G. intestinalis, Eimeria* sp., *Toxoplasma* sp., *Cryptosporidium parvum, C. muris, C. baileyi, C. meleagridis, C. wrairi,* and *C. nosarum*. Obtaining unique epitopes from these organisms by screening proteins and by assaying peptides in vitro are commonly known to those skilled in the art. In one aspect, the screening methods of the present invention can be used to identify peptides and/or target compounds with binding affinity to one or more of these organisms.

The term "antimicrobial compound" is art-recognized and is intended to include a compound which inhibits the proliferation or viability of a microbe which is undesirable and/or which disrupts a microbial cell. The language further includes diminishment of an activity which is undesirable and associated with the microbe. Examples include antibiotics, biocides, antibacterial compounds.

The term "antibiotics" is art recognized and includes antimicrobial agents synthesized by an organism in nature and isolated from this natural source, and chemically synthesized antibiotics. The term includes but is not limited to: polyether ionophore such as monensin and nigericin; macrolide antibiotics such as erythromycin and tylosin; aminoglycoside antibiotics such as streptomycin and kanamycin; β-lactam antibiotics such as penicillin and cephalosporin; and polypeptide antibiotics such as subtilisin and neosporin. Semi-synthetic derivatives of antibiotics, and antibiotics produced by chemical methods are also encompassed by this term. Non-limiting examples of antibiotics that can be used in combination with the peptides of the present invention are listed herein.

Chemically-derived antimicrobial agents such as isoniazid, trimethoprim, quinolines, and sulfa drugs are considered antibacterial drugs, although the term antibiotic has been applied to these. These agents and antibiotics have specific cellular targets for which binding and inhibition by the agent or antibiotic can be measured. For example, erythromycin, streptomycin and kanamycin inhibit specific proteins involved in bacterial ribosomal activity; penicillin and cephalosporin inhibit enzymes of cell wall synthesis; and rifampicin inhibits the β subunit of bacterial RNA polymerase. It is within the scope of the screens of the present invention to include compounds derived from natural products and compounds that are chemically synthesized.

The term "subject" refers to any living organism in which an immune response is elicited. The term refers to a living animal or human in need of treatment for, or susceptible to, a condition involving an unwanted or undesirable microorganism, e.g., a particular treatment for having an unwanted pathogenic cell as defined below. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term subject does not denote a particular age or sex. Thus, adult and newborn subjects, as well as fetuses, whether male or female, are intended to be covered. In preferred embodiments, the subject is a mammal, including humans and non-human mammals. In the most preferred embodiment, the subject is a human. The term "subject" does not preclude individuals that are entirely normal with respect to having an unwanted pathogen or normal in all respects. The subject may formerly have been treated with antibiotic or antimicrobial therapy, and may be under treatment, or have been treated by antibiotic or antimicrobial therapy in the past.

The term "patient," as used herein, refers to a human subject who has presented at a clinical setting with a particular symptom or symptoms suggesting one or more diagnoses of having an infectious disease, or having the presence of an unwanted microbial cell. A patient's diagnosis can alter during the course of disease progression, such as development of further disease symptoms, or remission of the disease, either spontaneously or during the course of a therapeutic regimen or treatment. Thus, the term "diagnosis" does not preclude different earlier or later diagnoses for any particular patient or subject. The term "prognosis" refers to assessment for a subject or patient of a probability of developing a condition associated with or otherwise indicated by presence of one or more unwanted pathogenic cells in the patient.

The invention is described in more detail in the following subsections:

I. Ribosome

The ribosome is the cellular machinery in charge of protein synthesis. Many antibiotics target the ribosome by interfering with the mechanism of protein synthesis. The widespread use of antibiotics has propelled the outburst of bacteria resistant to antibiotics. In one aspect, the invention identifies new ribosomal sites for antibiotic targeting.

Most of the antibacterial agents that inhibit protein synthesis interact with the bacterial ribosome. The differences between the composition of bacterial and mammalian ribosomes give these compounds their selectivity. For example, aminoglycosides are a group of structurally related compounds containing three linked hexose sugars. Aminoglycosides exert a bactericidal effect by binding irreversibly to the 30S subunit of the bacterial ribosomes and blocking initiation of protein synthesis. Macrolides and lincosamides, although structurally different, are two types of antibiotics that bind specifically to the 50S portion of the bacterial ribosome. Chloramphenicol also binds irreversibly to the 50S portion of the bacterial ribosome at a site close but not identical to the sites binding the macrolides and lincosamides. Tetracyclines interact reversibly with the bacterial 30S ribosomal subunit, blocking the binding of aminoacyl tRNA to the mRNA-ribosome complex. This mechanism is markedly different from that of the aminoglycosides, which also bind to the 30S subunit.

Translation of the genetic code occurs on the ribosome, a large nucleoprotein complex that consists of two subunits. In bacteria, the two subunits are denoted 30S and 50S. The 50S subunit contains the catalytic site of peptidyl transferase activity, while the 30S subunit plays a crucial role in decoding messenger RNA. The 30S ribosomal subunit is a major target for antibiotics. The ribosome is a useful target for antibiotics since the structure of the 30S is widely conserved between prokaryotes, allowing for broad spectrum antibiotics. However, resistance to current antibiotics is currently a major problem in the field of medicine. There are presently very few new antibiotics available which can be used to treat the highly resistant strains of bacteria such as MRSA (methicilin resistant *Staphylococcus aureus*) which are becoming increasingly widespread.

In one aspect, the invention identifies new ribosomal sites for antibiotic targeting. The stem-loop H18 in 16S rRNA from 30S ribosomal subunit plays a central role in the decoding of proteins, and folds into a pseudoknot whose disruption is detrimental for translation of proteins, leading to cell death. H18 is a very conserved region and mutations are detrimental for function, characteristic that has been observed for other critical functional centers of the ribosome, already being targeted by common antibiotics. H18 is an unexploited site, with potential for antibiotic action, it has not been targeted before, and no known antibiotic exists that bind this site. H18 will be a useful site for the development of new antibacterials, specially useful for superbugs that are resistant in some cases to all antibiotics known.

In one aspect, the invention provides a novel screening technique for selecting peptides with specific binding properties from a large library of random peptide motifs. A novel version of phage display is disclosed for identifying new peptides with binding affinity for new target sites in the ribosome. In some embodiments, peptides with affinity for a tertiary structural motif of the ribosomal RNA can be selected. In preferred embodiments, peptides with affinity for the stem-loop H18 of the 16S rRNA small subunit are identified. For example, peptides can be identified with a binding affinity greater than 30%, greater than 50%, greater than 60%, greater than 75%, and greater than 85%. In preferred embodiments, the peptides can inhibit protein synthesis. In some embodiments, the peptides can be used in antimicrobial and/or antibacterial compositions. In other embodiments, the peptides can be used to inhibit cancer cell proliferation. The peptides can be coupled to moieties, such that the peptides are specifically directed to a desired target cell. In yet other embodiments, the peptides can be used in screening assays. The peptides can be coupled to fluorescent molecules, radioactive isotopes, other antibiotics, crosslinking agents, and/or oligonucleotides.

In one aspect of the present invention, a novel methodology was developed to screen a library of peptides in order to find peptides with protein synthesis inhibiting properties. In some examples, the methods can be used to identify peptides that can bind to a prokaryotic ribosomal subunit and antibacterial properties. For example, peptides with binding affinity for H18. By means of this methodology, peptide inhibitors of protein synthesis were identified. The selected peptides show inhibitory activity in prokaryotic systems. In some embodiments, the peptides of the invention show protein synthesis inhibition in eukaryotes. These peptides can be used, for example, as anticancer agents. In some embodiments, the peptides can be attached to moiety capable of directing the peptide to a desired target cell.

In some other embodiments, the peptides can be used to stimulate protein synthesis. Stimulation of protein synthesis characteristic useful to enhance the yield of protein synthesis in cases in which the efficiency of synthesis is poor. The identified peptides exhibit synergy with other antibiotics, having the potential to be used in combination therapies or can be coupled with other antibiotics to improve potency. The peptides of the present invention can be used as leads to screen libraries of compounds targeting the new H18 site, helping in the task of finding new antibacterials with binding affinities for H18, and having the functional properties of being inhibitors of protein synthesis. The peptides of the present invention can be also used in detailed structure/activity relationship analysis to generate derivatives and new classes of antibacterials.

In another aspect, a method was developed to examine the binding of the discovered peptides to the ribosome by tagging the peptides to fluorescent molecules.

II. Novel Selection Technique

In one aspect of the invention, a phage display technique is disclosed for identifying new peptide ligands with binding affinity to new target sites in the ribosome. Phage display is a system in which a protein is displayed on the surface of a phage as a fusion with one of the coat proteins of the virus. The DNA that encodes this protein is housed within the virion. By cloning large numbers of DNA sequences into the phage, display libraries are produced with a repertoire of many billions of unique displayed proteins. Phage display can be used as a screening technique for selecting peptides with specific binding properties from a large library of random peptide motifs. Advantages of using phage display over other approaches for drug discovery are that the scale of the screening is much greater than when using chemical libraries, billions of phage are screened at the same time in comparison to thousands of compounds screened one by one; the affinity of the peptide over the target can be modulated, the screening can be done under specific conditions that will improve binding specificity, peptides can be selected by their binding and functional capabilities, and the cDNA is in the phage and thus no separate cloning step is required.

Ribosomal RNA folds into tertiary structural motifs that are excellent target for peptides, in particular the stem-loop H18 of the 16S rRNA small subunit is a new potential target for antibiotics. The stem-loop H18 RNA forms the higher order structure of a pseudoknot, generating a binding pocket capable of accommodating ligands such as peptides. Small peptides are unstructured in solution, and adopt a distinct fold when complexed with RNA, originating a conformational change in the RNA upon binding. The stem-loop H18 RNA is important for function in the synthesis of proteins and disruption of the secondary structure induced by a conformational change will lead to the inhibition of protein synthesis and as a consequence cell death. In some embodiments, the new target site can be combined with currently available drug targets such that new ligand peptides can be identified. This technique will delay the appearance of resistance for the newly discovered antibiotics.

Peptides with antibacterial activity targeting the stem-loop H18 RNA were identified using a newly developed protocol to select for phage displaying peptides that selectively bind the H18 RNA, site that has not been previously used for antibiotic screening. A 59-nt RNA-DNA construct representing the stem-loop H18 of *Bacillus anthracis* small ribosomal subunit (FIG. 1) was designed. Phage display technology faces the problem of phage having high affinity for plastics, wells, streptavidin and other materials used during the screening, we solved this problem as follows: first a counter selection was done against materials used for the affinity selection, and by optimization of the number and stringency of washes to remove unbound phage after each cycle of selection; second, the selection was done using a novel strategy in which the RNA target used for selection was a extended target molecule (e.g. hybrid RNA/DNA or hybrid RNA/organic molecule) and the extended target molecule (e.g. DNA or an organic molecule) was tagged with an affinity linker (e.g. biotin molecule), this system allows for the specific selection of phage binding to the RNA target; third, the isolation of phage bound to the RNA target was done with immobilized surfaces (e.g., magnetic beads or microtiter plates) coated with a binding partner of an affinity linker of the extended target molecule, and only phage bound to the RNA target are pulled out from solution; fourth, unbound phage are removed by a series of washes in the presence of a detergent that will remove any phage bound nonspecifically. The advantage of this novel design is the ability of releasing specific phage- RNA complexes obtained from the initial nonspecific pool of $2 \times 10^{11}$ phage. The specific phage-RNA complexes are released from the capture system (magnetic beads or wells) by the use of the enzyme (e.g., deoxyribonuclease I), that will digest only and specifically the extended target molecule (e.g. DNA portion of an RNA/DNA hybrid). Therefore the phage with affinity to the H18 RNA are liberated and ready to be used for further selection steps.

Figure 2A:
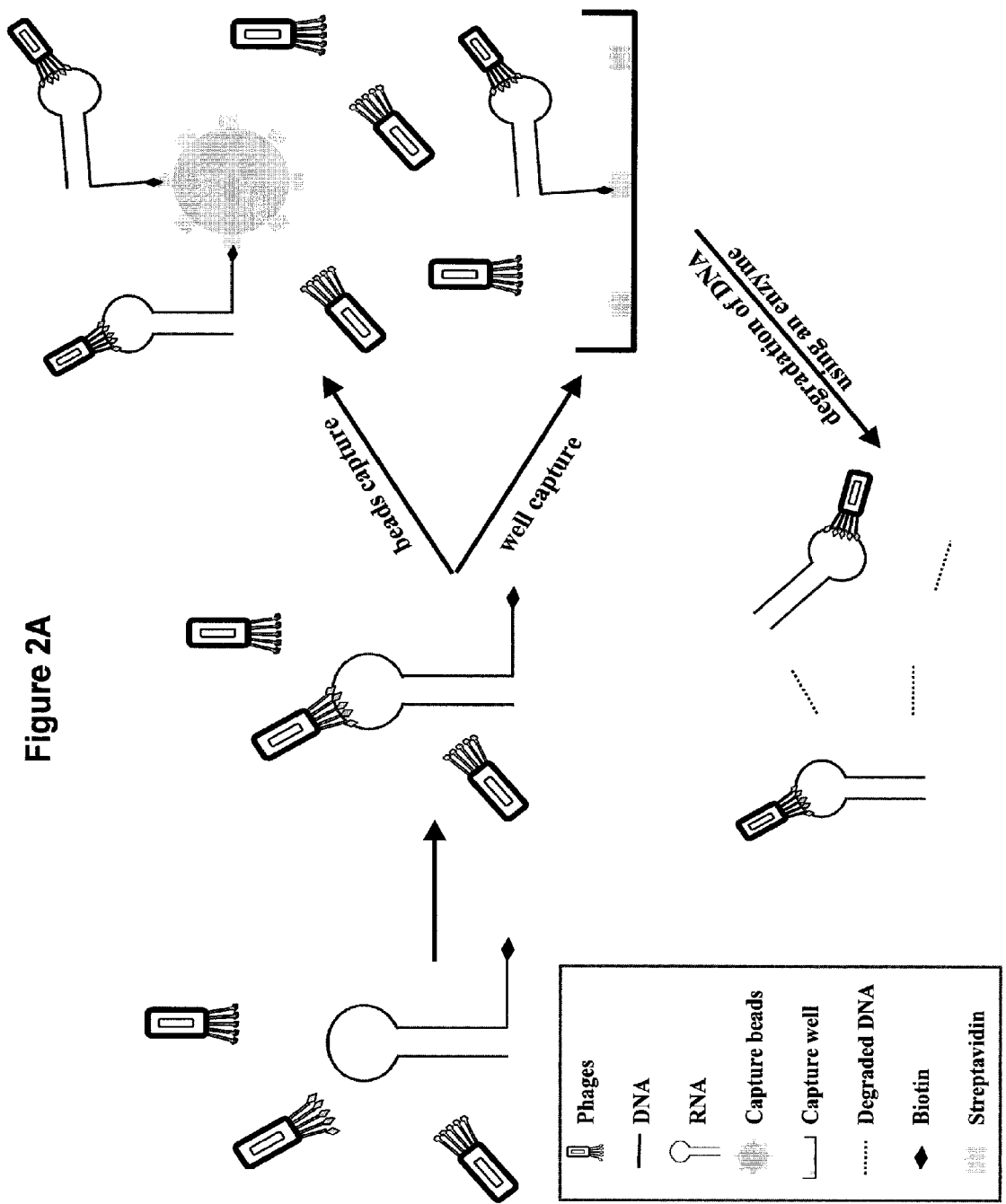
FIG. 2A is a schematic diagram of an exemplary selection scheme used for affinity selection.
Figure 2B:
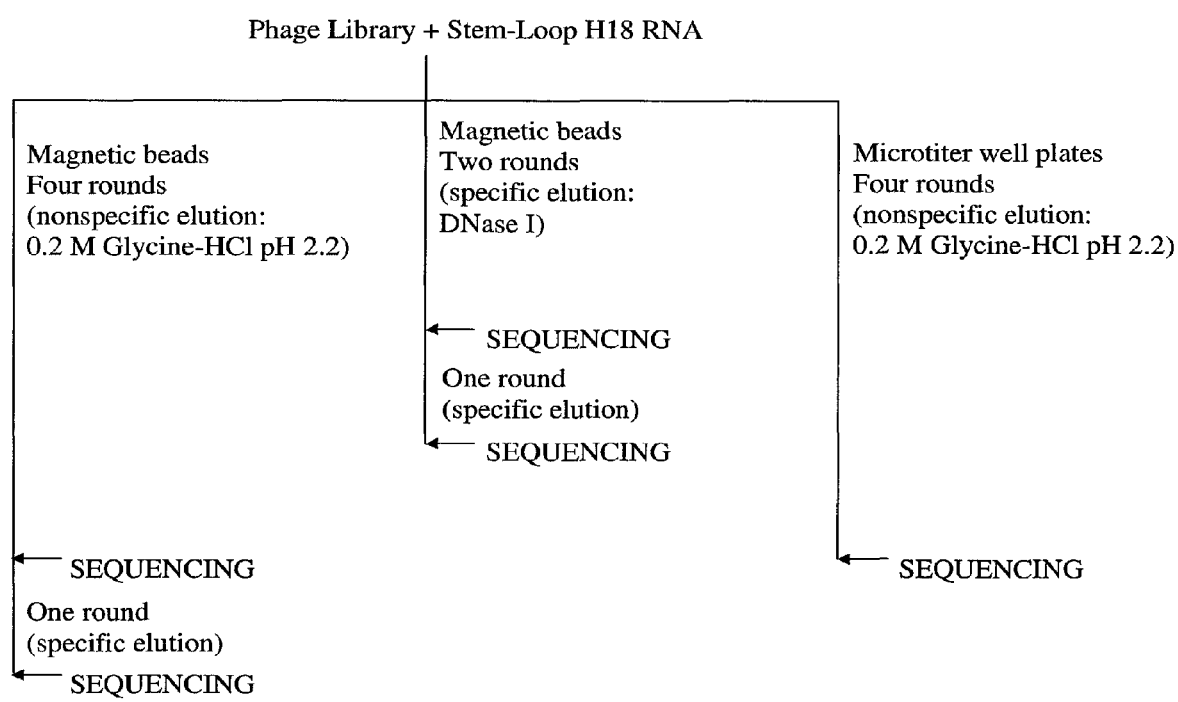
FIG. 2B is a schematic of an exemplary selection scheme used for affinity selection.

A general description of a screening method of the present invention is graphically depicted in FIGS. 2A and 2B and described below. Example 2 demonstrates that the methods of the present invention can be used to identify test compounds, i.e., peptides with affinity for a ribosomal subunit. The affinity selection methodology was designed and developed using the two capture formats of magnetic beads and microtiter plates, and two elution systems including nonspecific elution, and specific elution by enzymatic digestion of the specifically designed poly-dA tail of H18 RNA with DNase I. H18 RNA at a concentration of 100 nM was allowed to interact with the phage library in solution in the presence of tRNA (2 μg/μL). The RNA-binding phage were captured using either capture format, and biotin was added to a final concentration of 0.1 mM in order to displace any streptavidin-binding phage from the solid support. Unbound phage were washed from the solid support with wash buffer supplemented with tween-20. The stringency of washes was increased for the magnetic beads capture system, by increasing the concentration of tween-20 from 0.1% to 0.5% after the first round of selection. The stringency of washes for the microtiter well plate system was kept constant throughout the rounds of selection by using a concentration of tween-20 of 0.05%. The bound phage were released from the solid support using an acidic buffer as a nonspecific eluant. After four rounds of selection the sequences of the phage-displayed peptides were obtained by sequencing of the phage DNA.

An additional round of selection was performed using the amplified eluate from the fourth round of magnetic beads selection. The bound phage were eluted by using an enzyme capable of cleaving the extention moiety. A separate affinity selection was carried out using an immobilized capture system and eluting the bound phage specifically with an enzyme. An overview of an example of the selection process is shown in FIGS. 2A and B.

II. Synergism and Combinations with Antibiotics

Currently, there are several types of antibiotic compounds in use against bacterial pathogens, and these compounds act through a variety of anti-bacterial mechanisms. In one aspect, the identified peptides can be used in combination with other antibiotics. In some embodiment, new ribosomal sites can be targeted in combination with new or current antibacterial or antimicrobial agents. Combination therapy can help delay new resistance mechanisms.

Drug combinations are known to reduce the dosages required, and in some cases, produce synergistic effects. Thus, in order to increase the effectiveness of the peptide therapies described herein, it may be desirable to combine these compositions with other agents effective in the treatment of bacterial infections, such as antibiotics.

An "antibiotic" agent is capable of negatively affecting bacterial growth in a subject, for example, by killing bacterial cells, reducing the growth rate of bacterial cells, or otherwise increasing the quality of life of the afflicted subject. This process may involve contacting the cells with the peptide the agent(s) at the same time. This may be achieved by contacting the cell with a single composition or pharmacological formulation that includes both the peptide and the antibiotic, or by contacting the cell with two distinct compositions or formulations, at the same time, wherein one composition includes the peptide and the other includes the second agent(s).

Alternatively, the peptide therapy may precede or follow the other agent treatment by intervals ranging from minutes to weeks. In embodiments where the other agent and peptide are applied separately to the cell, one would generally ensure that a significant period of time did not expire between the time of each delivery, such that the agent and peptide would still be able to exert an advantageously combined effect on the cell. In such instances, it is contemplated that one may contact the cell with both modalities within about 1224 h of each other and, more preferably, within about 612 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Administration of the peptides of the present invention to a patient will follow general protocols for the administration of antibiotics, taking into account the toxicity, if any. It is expected that the treatment cycles would be repeated as necessary.

Various classes of antibiotics that can also be used in combination with the invention are described below. For example, beta-lactam antibiotics, such as penicillin and cephalosporin, act to inhibit the final step in peptidoglycan synthesis. Glycopeptide antibiotics, including vancomycin and teichoplanin, inhibit both transglycosylation and transpeptidation of muramyl-pentapeptide, again interfering with peptidoglycan synthesis. Other well-known antibiotics include the quinolones, which inhibit bacterial DNA replication, inhibitors of bacterial RNA polymerase, such as rifampin, and inhibitors of enzymes in the pathway for production of tetrahydrofolate, including the sulfonamides.

Antibacterial agents, like all anti-microbial drugs, are directed against unique targets not present in mammalian cells. The goal is to limit toxicity to the host and maximize chemotherapeutic activity affecting invading microbes only. One major difference between bacterial and mammalian cells is the presence in bacteria of a rigid wall external to the cell membrane. The wall protects bacterial cells from osmotic rupture because of the difference between the hyperosmolar (up to 20 atm) cell interior and the usually isosmolar or hyposmolar host environment. In both gram-positive and gram-negative bacteria, peptidoglycan, a large, covalently linked sacculus that surrounds the bacterium, is the structure that confers cell wall rigidity and resistance to osmotic lysis. In gram positive bacteria, peptidoglycan is the only later external to the cell membrane and is thick (20 to 80 nm); while in gram-negative bacteria the peptidoglycan layer is thin (1 nm) and is protected by an outer membrane. Chemotherapeutic agents directed at any stage of the synthesis, export, assembly, or cross-linking of peptidoglycan inhibit bacterial cell growth and, in most cases, lead to cell death.

Bacitracin, a cyclic peptide antibiotic, inhibits the conversion to its active form of the lipid carrier that moves the water-soluble cytoplasmic peptidoglycan subunits through the cell membrane to the cell exterior. Cell wall subunits accumulate in the cytoplasm and can be added to the growing peptidoglycan chain.

Cyclopeptides, (such as vancomycin and teichoplanin) are high molecular weight antibiotics that bind to the terminal D-alanine-D-alanine component of the stem peptide when the subunits are external to the cell membrane and still linked to the lipid carrier. This binding sterically inhibits the addition of sub units to the peptidoglycan backbone.

β-Lactam antibiotics, such as penicillins, cephalosporins, carbapenems, and monobactams, characterized by a fourmembered β-Lactam ring, prevent the cross-linking reaction called transpeptidation. Energy for attaching a peptide cross-bridge from the stem peptide of one peptidoglycan subunit to another is derived from the cleavage of a terminal D-alanine residue from the subunit stem peptide. The β-Lactam ring of the antibiotic forms an irreversible covalent acyl bond with the transpeptidase enzyme, preventing the cross-linking reaction. Transpeptidases and similar enzymes involved in cross-linking are called penicillin-binding proteins because they have active sites that bind β-Lactam antibiotics.

Virtually all the antibiotics that inhibit bacterial cell wall synthesis are bactericidal, eventually resulting in the cell's death due to osmotic lysis. However, much of the loss of cell wall integrity following treatment with cell-active agents is due to the bacteria's own cell wall-remodeling enzymes (autolysins) that cleave peptidoglycan bonds in the normal course of cell growth. Autolysis without normal cell wall repair results in weakness and eventual cell death.

Some classes of antibiotics act at the level of protein synthesis. Notable among these are the aminoglycosides, such as kanamycin and gentamycin. This class of compounds targets the bacterial 30S ribosome subunit, preventing the association with the 50S subunit to form functional ribosomes. Tetracyclines, another important class of antibiotics, also target the 30S ribosome subunit, acting by preventing alignment of aminoacylated tRNA's with the corresponding mRNA codon. Macrolides and lincosamides, another class of antibiotics, inhibit bacterial synthesis by binding to the 50S ribosome subunit, and inhibiting peptide elongation or preventing ribosome translocation.

The antimetabolites are all synthetic compounds that interfere with bacterial synthesis of folic acid. Products of the folic acid synthesis pathway function as coenzymes for the one-carbon transfer reactions that are essential for the synthesis of thymidine, all purines, and several amino acids. Inhibition of folate synthesis leads to cessation of cell growth and in some cases, to bacterial cell death. The principal antibacterial antimetabolites are sulfonamides and trimethoprim.

Numerous additional antibacterial compounds have disparate effects on nucleic acids. The quinolones, including nalidixic acid and its fluorinated derivatives, are synthetic compounds that inhibit the activity of the A subunit of the bacterial enzyme DNA gyrase, which is responsible for negative supercoiling of DNA during replication in the intact cell. The antibiotic novobiocin also interferes with the activity of DNA gyrase, but it interferes with the B subunit. Rifampin, used primarily as an antituberculosis agent, binds tightly to bacterial DNA-dependent RNA polymerase, thus inhibiting transcription of DNA into RNA, and nitrofurantoin, a synthetic compound, causes DNA damage, being reduced by a bacterial enzyme to highly reactive, short-lived intermediates that are thought to cause DNA strand breakage.

Still other compounds cause alternation of cell membrane permeability. The polymyxins behave as cationic, surface-active compounds that disrupt the permeability of both the outer and the cytoplasmic membranes of gram-negative bacteria. Gramicidin A, on the other hand, acts as an ionophore, forming pores or channels in lipid bilayers.

One major and important class of genes consists of those bacterial genes that are essential for growth or viability of a bacterium. Because useful conventional antibiotics, such as those described above, are known to act by interfering with the products of essential genes, it is likely that the discovery of new essential gene products will have a significant impact on efforts to develop novel antimicrobial drugs.

Conditional mutations such as temperature or suppressor sensitive mutations have been used in the past to identify some of the essential genes in bacteria. However, not all essential genes can be identified by these types of mutations. The limitation is due to the fact that these conditional mutations must occur at a specific codon of the genes in order to alter the coded amino acid of the protein. Therefore, the occurrence of mutants with these phenotypes is expected to be low. Moreover, not all of the gene can be converted to conditional mutations; there may be no codon causing these mutations in their nucleotide sequences.

Essential gene products have been traditionally identified through the isolation of conditional lethal mutants, or by transposon mutagenesis in the presence of a complementing wild type allele (balanced lethality). However, such approaches are laborious, as they require identification, purification, and study of individual mutant strains. These methods are also limited to species with well-developed systems for genetic manipulation and, therefore, cannot be readily applied to many of the potentially dangerous microorganisms whose genomes have recently been sequenced.

For example, conditional mutations such as temperature or suppressor sensitive mutations have been used in the past to identify some of the essential genes in bacteria. However, not all of the essential genes can be identified by these types of mutations because the conditional mutation must occur at a specific codon of the genes in order to alter the coded amino acid of the protein. Therefore, the occurrence of mutants with these phenotypes is expected to be low. Moreover, not all of the gene can be converted to conditional mutations; there may be no codon causing the conditional mutation in the nucleotide sequences of the bacterial genome.

III. Antimicrobial Compound Compositions and Uses

The invention provides pharmaceutically acceptable compositions which include a therapeutically-effective amount or dose of an antimicrobial compound, e.g., peptides from Tables 1 and 2, and one or more pharmaceutically acceptable carriers (additives) and/or diluents. A composition can also include a second antimicrobial agent, e.g., an inhibitor of an efflux pump. In some embodiments, the peptides of the present invention can be coupled to moieties, such that the peptides can be directed to a target cell. The invention identifies a method of inhibiting protein synthesis in a cell comprising administering a compound capable interacting with a ribosome at a stem-loop H18 in 16S rRNA of a 30S ribosomal subunit.

In preferred embodiments compounds of the invention can be used to inhibit the growth of an unwanted organism, e.g., an infectious, pathogenic organism or an organism that causes spoilage or biofouling, by contacting the organism with the compound. The compound can be applied prior infection by the organism to prevent a subject from becoming infected. For example, the compounds can be used for cleaning surfaces, e.g., counter tops, instruments, or the skin of the subject, to inhibit the growth of the organism and reduce the possibility of the subject actually becoming infected with one of the organisms.

Treating or treatment of a state characterized by the presence of an unwanted cell, e.g., an unwanted pathogenic cell, e.g., an unwanted bacterium, is intended to include the alleviation of or diminishment of at least one symptom, for example, fever or inflammation, typically associated with the state. The treatment also includes alleviation or diminishment of more than one symptom. Preferably, the treatment cures, e.g., substantially eliminates, the symptoms associated with the state.

The terms "therapeutically effective dose" or "therapeutically effective amount" of a compound or peptide described herein, is that amount necessary or sufficient to perform its intended function, e.g., on a surface or on or within a subject, e.g., to eradicate or inhibit growth of an unwanted pathogen, e.g., microorganism. The therapeutically effective amount can vary depending on such factors as the species or strain of the pathogen, the amount of the pathogen to be inhibited ant the manner in which the compound is to be used. One of ordinary skill in the art would be able to study the aforementioned factors and make a determination regarding the effective amount of the compound required without undue experimentation. For administration, one of ordinary skill in the art would be able to determine such amounts based on such factors as the subject's size, the severity of the subject's symptoms, and the particular composition or route of administration selected. An in vitro or in vivo assay can be here used to determine an "effective amount" of the compounds described herein to achieve inhibition of growth or proliferation of the cell by binding and inhibiting the specific target.

A "therapeutically effective dosage" is a dosage of a compound that preferably inhibits growth of an unwanted pathogenic cell, or destroys cell viability, by at least about 50%, more preferably by at least about 80%, even more preferably by at least about 90%, and still more preferably by at least about 95% relative to the absence of the compound. The ability of a compound to inhibit or kill infectious disease cells can be evaluated in an in vitro inhibitory concentration assay, or, e.g., an animal model system predictive of efficacy in infectious diseases. Alternatively, this property of a compound can be evaluated by examining the ability of the compound to inhibit in vitro by using assays well-known to the skilled practitioner. Assays include the of effect on viability of the test pathogenic cell, by assay of quantity of "colony forming units" (cfu), in the presence and absence of the compound; assay of capability to carry out a physiological process, such as cellular uptake of a metabolite; assay of uptake and incorporation of a metabolite into a macromolecule, such as a nucleic acid or protein; each assay conducted in the presence of a range of concentrations and in the absence of the compound. For compounds having a known specific target, the effective dosage to inhibit the activity of that target, such as an enzyme, can be assessed using isolated target material. In addition, the antimicrobial agents and compounds of the invention can also be used, for example, in antimicrobial soap or detergent preparations.

IV. Pharmaceutical Compositions

As described in detail below, the pharmaceutical compositions can be formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream, foam, or suppository; or (5) aerosol, for example, as an aqueous aerosol, liposomal preparation or solid particles containing the compound.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the antimicrobial agents or compounds of the invention from one organ, or portion of the body, to another organ, or portion of the body without affecting its biological effect. Each carrier should be "acceptable" in the sense of being compatible with the other ingredients of the composition and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical compositions. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Pharmaceutical compositions of the present invention may be administered to epithelial surfaces of the body orally, parenterally, topically, rectally, nasally, intravaginally, intracisternally. They are of course given by forms suitable for each administration route. For example, they are administered in tablets or capsule form, by injection, inhalation, eye lotion, ointment, etc., administration by injection, infusion or inhalation; topical by lotion or ointment; and rectal or vaginal suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a sucrose octasulfate and/or an antibacterial or a contraceptive agent, drug or other material other than directly into the central nervous system, such that it enters the subject's system and, thus, is subject to metabolism and other like processes, for example, subcutaneous administration.

In some methods, the compositions of the invention can be topically administered to any epithelial surface. An "epithelial surface" according to this invention is defined as an area of tissue that covers external surfaces of a body, or which and lines hollow structures including, but not limited to, cutaneous and mucosal surfaces. Such epithelial surfaces include oral, pharyngeal, esophageal, pulmonary, ocular, aural, nasal, buccal, lingual, vaginal, cervical, genitourinary, alimentary, and anorectal surfaces.

Compositions can be formulated in a variety of conventional forms employed for topical administration. These include, for example, semi-solid and liquid dosage forms, such as liquid solutions or suspensions, suppositories, douches, enemas, gels, creams, emulsions, lotions, slurries, powders, sprays, lipsticks, foams, pastes, toothpastes, ointments, salves, balms, douches, drops, troches, chewing gums, lozenges, mouthwashes, rinses.

Conventionally used carriers for topical applications include pectin, gelatin and derivatives thereof, polylactic acid or polyglycolic acid polymers or copolymers thereof, cellulose derivatives such as methyl cellulose, carboxymethyl cellulose, or oxidized cellulose, guar gum, acacia gum, karaya gum, tragacanth gum, bentonite, agar, carbomer, bladderwrack, ceratonia, dextran and derivatives thereof, ghatti gum, hectorite, ispaghula husk, polyvinypyrrolidone, silica and derivatives thereof, xanthan gum, kaolin, talc, starch and derivatives thereof, paraffin, water, vegetable and animal oils, polyethylene, polyethylene oxide, polyethylene glycol, polypropylene glycol, glycerol, ethanol, propanol, propylene glycol (glycols, alcohols), fixed oils, sodium, potassium, aluminum, magnesium or calcium salts (such as chloride, carbonate, bicarbonate, citrate, gluconate, lactate, acetate, gluceptate or tartrate).

Such compositions can be particularly useful, for example, for treatment or prevention of an unwanted cell, e.g., vaginal *Neisseria gonorrhea*, or infections of the oral cavity, including cold sores, infections of eye, the skin, or the lower intestinal tract. Standard composition strategies for topical agents can be applied to the antimicrobial compounds, e.g., compounds of the present invention, i.e., peptides of Tables 1 and 2 or a pharmaceutically acceptable salt thereof in order to enhance the persistence and residence time of the drug, and to improve the prophylactic efficacy achieved.

For topical application to be used in the lower intestinal tract or vaginally, a rectal suppository, a suitable enema, a gel, an ointment, a solution, a suspension or an insert can be used. Topical transdermal patches may also be used. Transdermal patches have the added advantage of providing controlled delivery of the compositions of the invention to the body. Such dosage forms can be made by dissolving or dispersing the agent in the proper medium.

Compositions of the invention can be administered in the form of suppositories for rectal or vaginal administration. These can be prepared by mixing the agent with a suitable non-irritating carrier which is solid at room temperature but liquid at rectal temperature and therefore will melt in the rectum or vagina to release the drug. Such materials include cocoa butter, beeswax, polyethylene glycols, a suppository wax or a salicylate, and which is solid at room temperature, but liquid at body temperature and, therefore, will melt in the rectum or vaginal cavity and release the active agent.

Compositions which are suitable for vaginal administration also include pessaries, tampons, creams, gels, pastes, foams, films, or spray compositions containing such carriers as are known in the art to be appropriate. The carrier employed in the sucrose octasulfate/contraceptive agent should be compatible with vaginal administration and/or coating of contraceptive devices. Combinations can be in solid, semi-solid and liquid dosage forms, such as diaphragm, jelly, douches, foams, films, ointments, creams, balms, gels, salves, pastes, slurries, vaginal suppositories, sexual lubricants, and coatings for devices, such as condoms, contraceptive sponges, cervical caps and diaphragms.

For ophthalmic applications, the pharmaceutical compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the compositions can be formulated in an ointment such as petrolatum. Exemplary ophthalmic compositions include eye ointments, powders, solutions and the like.

Powders and sprays can contain, in addition to sucrose octasulfate and/or antibiotic or contraceptive agent(s), carriers such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Compositions of the invention can also be orally administered in any orally-acceptable dosage form including, but not limited to, capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of sucrose octasulfate and/or antibiotic or contraceptive agent(s) as an active ingredient. A compound may also be administered as a bolus, electuary or paste. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Tablets, and other solid dosage forms, such as dragees, capsules, pills and granules, may be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the antimicrobial agent(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Sterile injectable forms of the compositions of this invention can be aqueous or oleaginous suspension. These suspensions may be formulated according to techniques known in the art using suitable dispersing or wetting agents and suspending agents. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The antimicrobial agent or a pharmaceutically acceptable salt thereof will represent some percentage of the total dose in other dosage forms in a material forming a combination product, including liquid solutions or suspensions, suppositories, douches, enemas, gels, creams, emulsions, lotions slurries, soaps, shampoos, detergents, powders, sprays, lipsticks, foams, pastes, toothpastes, ointments, salves, balms, douches, drops, troches, lozenges, mouthwashes, rinses and others. Creams and gels for example, are typically limited by the physical chemical properties of the delivery medium to concentrations less than 20% (e.g., 200 mg/gm). For special uses, far less concentrated preparations can be prepared, (e.g., lower percent formulations for pediatric applications). For example, the pharmaceutical composition of the invention can comprise sucrose octasulfate in an amount of 0.001-99%, typically 0.01-75%, more typically 0.1-20%, especially 1-10% by weight of the total preparation. In particular, a preferred concentration thereof in the preparation is 0.5-50%, especially 0.5-25%, such as 1-10%. It can be suitably applied 1-10 times a day, depending on the type and severity of the condition to be treated or prevented.

Given the low toxicity of an antimicrobial agent or a pharmaceutically acceptable salt thereof over many decades of use as a biocide [W. R. Garnett, Clin. Pharm. 1:307-314 (1982); R. N. Brogden et al., Drugs 27:194-209 (1984); D. M. McCarthy, New Eng J Med., 325:1017-1025 (1991), an upper limit for the therapeutically effective dose is not a critical issue. For most forms of compounds of the present invention, i.e., peptides of Tables 1 and 2 the minimum amount present in the materials forming combinations of this invention that is effective in treating or preventing bacterial disease due to direct interaction with the organism should produce be less than 0.1 µg/ml, less than 0.5 µg/ml, preferably less than 1 µg/ml, even more preferably less than less than 5 µg/ml, and most preferably less than 10 µg/ml.

For prophylactic applications, the pharmaceutical composition of the invention can be applied prior to physical contact. The timing of application prior to physical contact can be optimized to maximize the prophylactic effectiveness of the compound. The timing of application will vary depending on the mode of administration, the epithelial surface to which it is applied, the surface area, doses, the stability and effectiveness of composition under the pH of the epithelial surface, the frequency of application, e.g., single application or multiple applications. Preferably, the timing of application can be determined such that a single application of composition is sufficient. One skilled in the art will be able to determine the most appropriate time interval required to maximize prophylactive effectiveness of the compound.

One of ordinary skill in the art can determine and prescribe the effective amount of the pharmaceutical composition required. For example, one could start doses at levels lower than that required in order to achieve the desired therapeutic effect and gradually increase the dosage until the desired effect is achieved. In general, a suitable daily dose of a composition of the invention will be that amount of the composition which is the lowest dose effective to produce a therapeutic effect. Such an effective dose will generally depend upon the factors described above. It is preferred that administration be intravenous, intracoronary, intramuscular, intraperitoneal, or subcutaneous.

The practice of the present invention will employ, unless otherwise indicated, conventional techniques of cell biology, cell culture, molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, J. et al. (Cold Spring Harbor Laboratory Press (1989)); Short Protocols in Molecular Biology, 3rd Ed., ed. by Ausubel, F. et al. (Wiley, NY (1995)); DNA Cloning, Volumes I and II (D. N. Glover ed., 1985); Oligonucleotide Synthesis (M. J. Gait ed. (1984)); Mullis et al. U.S. Pat. No. 4,683,195; Nucleic Acid Hybridization (B. D. Hames & S. J. Higgins eds. (1984)); the treatise, Methods In Enzymology (Academic Press, Inc., N.Y.); Immunochemical Methods In Cell And Molecular Biology (Mayer and Walker, eds., Academic Press, London (1987)); Handbook Of Experimental Immunology, Volumes I-IV (D. M. Weir and C. C. Blackwell, eds. (1986)); and Miller, J. Experiments in Molecular Genetics (Cold Spring Harbor Press, Cold Spring Harbor, N.Y. (1972)).

The invention provides pharmaceutically acceptable compositions which include a therapeutically-effective amount or dose of an antimicrobial compound, e.g., peptides from Tables 1 and 2, and one or more pharmaceutically acceptable carriers (additives) and/or diluents. A composition can also include a second antimicrobial agent, e.g., an inhibitor of an efflux pump.

One skilled in the art will appreciate further features and advantages of the invention based on the above-described embodiments. Accordingly, the invention is not to be limited by what has been particularly shown and described, nor by the examples set forth below, except as indicated by the appended claims. All publications and references cited herein are expressly incorporated herein by reference in their entirety.

EXAMPLES

This invention is further illustrated by the following examples which should not be construed as limiting. The following experiments were performed to demonstrate various aspects of the invention.

Example 1

Materials and Methods (i) Materials

Target RNA. The RNA used as a target to select for peptide binding was a 59-nt RNA-DNA construct representing the stem-loop H18 of *Bacillus anthracis* small ribosomal subunit, H18 RNA (5'-GGGGCCACGGCUAACUACGUGCCAG-CAGCCGCGGUAA UACGUAGGUG-GCdAdAdAdAdAdAdAdAdAdABiotin-3') (Seq. ID. NO: 1). Three additional guanosines were added at the 5'end, and a poly-dA tail of 10 nucleotides followed by a biotin molecule was added at the 3'end. The RNA-DNA hybrid was obtained from Dharmacon RNA Technologies and purified by gel electrophoresis on denaturing (8 M urea) 8% polyacrylamide gels. H18 RNA was renatured in 80 mM HEPES-KOH pH 7.4, the RNA was incubated at 90° C. for 1 min in a water bath and allowed to cool down to 20° C. for 2 h.

(ii) Screening of Phage-Displayed Peptide Library.

The Ph.D.-7 phage library from New England Biolabs was used, which contains a library of $1.28\times10^9$ random heptapetides fused to coat protein pIII of M13 Phage. Two parallel selections were performed, one selection was done on microplates coated with streptavidin and another selection was done on streptavidin coated magnetic beads.

(iii) Selection on Streptavidin Coated Microplates.

Streptavidin coated plates from Pierce Biotechnology were washed four times with 250 μL of 1× wash buffer for wells (80 mM HEPES-KOH pH 7.4, 150 mM KCl, 20 mM $MgCl_2$, 0.05% tween-20 [v/v]), allowing 3 min incubation between washes. The plates were washed twice with 250 μL of 1× binding buffer (80 mM HEPES-KOH pH 7.4, 150 mM KCl, 20 mM $MgCl_2$). Before starting the selection step a counter selection was made against streptavidin and plastic. The phage ($2\times10^{11}$ phage) without target RNA were added to a washed well with 1× binding buffer, and incubated at 4° C. for 1 h. After the counter selection, selection was started by transferring the phage to a tube containing 80 mM HEPES-KOH pH 7.4, 150 mM KCl, 20 mM $MgCl_2$, 100 nM H18 RNA, 100 μg tRNA, and 40 U RNase Inhibitor. The mixture was incubated at 25° C. for 30 min, and then transferred to a washed well and incubated at 4° C. for 1 h. In order to compete out phage binding to streptavidin, biotin at a concentration of 0.1 mM was added and the wells were incubated at 4° C. for 5 min. The supernatant containing the unbound phage was removed and the wells were washed four times with 250 μL of 1× wash buffer for wells, and twice with 1× binding buffer. The H18 RNA-bound phage were eluted by adding 100 μL of 0.2 M glycine-HCl pH 2.2, 1 mg/ml BSA, incubated at 25° C. for 10 min, and neutralized with 15 μL of 1M Tris-HCl pH 9.1. The selected phage were amplified and titered. After four rounds of selection, the phage were cloned, individually amplified and sequenced.

(iv) Selection on Streptavidin Coated Magnetic Beads.

Magnetic beads Dynabeads M-280 streptavidin from Dynal Biotech were used. The magnetic beads (50 μL) were washed twice with 200 μL of a solution containing 0.1 M NaOH, and 0.05 M NaCl, then the beads were washed once with 200 μL of 0.1 M NaCl. Five washes with 200 μL of 1× binding buffer were performed. The beads were incubated for 3 min with shaking between washes. A counter selection was made against streptavidin and plastic, by incubating the washed magnetic beads with $2\times10^{11}$ phage at 25° C. for 30 min. The unbound phage were transferred to a tube containing 80 mM HEPES-KOH pH 7.4, 150 mM KCl, 20 mM $MgCl_2$, 100 nM H18 RNA, 100 μg tRNA, and 40 U RNase Inhibitor. The mixture was incubated at 25° C. for 30 mM, and in order to separate H18 RNA-bound phage and unbound phage the mixture was incubated with 50 μL of washed magnetic beads at 25° C. for 30 min. Biotin at a concentration of 0.1 mM was added and the beads were incubated at 25° C. for 5 min. The unbound phage were removed, and the beads were washed five times with 200 μL of 1× wash buffer for beads (80 mM HEPES-KOH pH 7.4, 150 mM KCl, 20 mM $MgCl_2$, 0.1% tween-20 [v/v]), and three times with 200 μL of 1× binding buffer. The H18 RNA-bound phage were eluted with 100 μL it of 0.2 M glycine-HCl pH 2.2, 1 mg/ml BSA, at 25° C. for 10 mM, and neutralized with 15 μL of 1 M Tris-HCl pH 9.1. The selected phage were amplified and titered. Four rounds of selection were performed, increasing stringency of washes for rounds two trough four by raising the concentration of tween-20 (v/v) in the wash buffer from 0.1% to 0.5%. The phage were cloned, individually amplified and sequenced. A fifth round of selection was performed, eluting the H18 RNA-bound phage by enzymatic degradation of the poly-dA tail with 250 U of DNase I from Fermentas Inc., at 37° C. for 30 min, then 1 μL of 0.5 M EDTA pH 8.0 was added. The phage were cloned, amplified and sequenced.

A separate panning was performed doing three rounds of selection, and eluting the bound phage using DNase I. Counter-selected phage were incubated with 80 mM HEPES-KOH pH 7.4, 150 mM KCl, 20 mM $MgCl_2$, 250 nM H18 RNA, 100 μg tRNA, and 40 U RNase Inhibitor, at 25° C. for 30 min. The mixture was added to washed beads and incubated at 25° C. for 30 min. Biotin at a concentration of 0.1 mM was added and incubated at 25° C. for 5 min. The beads were washed five times with 200 μL of 1× wash buffer for beads with 0.05% tween-20 (v/v), three times with 200 μL of 1× binding buffer, once with 300 μL of 1× reaction buffer for DNase I from Fermentas Inc., and the H18 RNA-bound phage eluted with 250 U of DNase I at 37° C. for 30 min, then 1 μL of 0.5 M EDTA pH 8.0 was added. The phage were cloned, amplified and sequenced after rounds two and three.

(v) Peptide Synthesis.

Select peptides were chemically synthesized by SynPep Corporation, and Sigma-Genosys with amidated C-termini and acetylated N-termini.

(vi) *E. coli* Transcription/Translation Assay.

*E. coli* S30 extract system for Circular DNA was used from Promega. Experiments were carried out in 96-well conical 0.2 mL plates from DOT Scientific Inc., in a final volume of 10 μL. S30 extract (3 μL) was preincubated in the 96-well plates with 1 μL of water or peptides in a range of concentrations at 25° C. for 5 mM. Translation mix (6 μL) containing 0.7 μg of pBESTluc™ DNA, 1 mM amino acid mixture without methionine (0.8 μL), S30 premix (4.0 μL), and 2.5 pmol [$^{35}$S]methionine (1175 Ci/mmol) from MB Biomedicals was added to each well and incubated at 37° C. for 5 min, then placed on ice. A solution of 1 M NaOH was added to the wells (245 μL) and incubated at 37° C. for 10 min. Synthesized protein was precipitated by addition of 1 ml of ice-cold 25% trichloroacetic acid (TCA)/2% casamino acids, and incubation on ice for 30 min. The samples were filtered on glass fiber filters pre-wetted with 5% TCA. The filters were washed three times with 5% TCA and once with acetone, dried and subjected to scintillation counting.

(vii) Eukaryotic Translation Assay.

The Promega flexi-rabbit reticulocyte lysate system was used. Experiments were carried out in 96-well conical 0.2 mL plates from DOT Scientific Inc., in a final volume of 10 μL. Rabbit Reticulocyte Lysate (7 μL) was incubated with 1 μL of water or peptides in a range of concentrations at 25° C. for 5 min. Luciferase Control RNA (Promega) was denatured before use by incubating the RNA at 65° C. for 3 min, and immediately placed on ice. Translation mix (2 μL) containing 0.3 μg of denatured Luciferase Control RNA, 1 mM amino acid mixture without methionine (0.3 μL), 6.7 pmol [$^{35}$S] methionine (1175 Ci/mmol) from MB Biomedicals, 8 U Ribonuclease Inhibitor (Roche), and 2.5 M potassium chloride (0.4 μL) was added to each well and incubated at 30° C. for 20 min. The translation reaction was stopped by adding 10 μL of cyclohexamide solution (100 μg/ml) and placing the wells on ice. The translation assays were transferred to tubes containing 245 μL of 1 M NaOH and incubated at 37° C. for 10 min. Synthesized protein was precipitated by addition of 1 ml of ice-cold 25% trichloroacetic acid (TCA)/2% casamino acids, and incubation on ice for 30 min. The samples were filtered on glass fiber filters pre-wetted with 5% TCA. The filters were washed three times with 5% TCA and once with acetone, dried and subjected to scintillation counting.

(viii) Synergy Activity Testing of Peptides with Antibiotics.

Stock solutions of peptides and antibiotics were prepared and serial twofold dilutions were made containing twice the desired final concentration. Drug combinations were prepared in 96-well conical 0.2 ml plates, and 1 μL of each combination was tested in the E. coli transcription/translation assay as described.

(ix) Determination of Peptide Dissociation Constants by Fluorescence Spectroscopy Using 30S Ribosomal Subunits and Peptides Fluorescently Labeled.

30S subunits were obtained from E. coli MRE600, and purified by 10-40% (w/v) sucrose gradient. Peptides were chemically synthesized by Sigma-Genosys, with amidated C-termini and a dansyl group at the N-termini. Fluorescent peptide solution for titration was prepared at a concentration of 1 μM in TNM buffer (50 mM Tris-HCl pH 7.6, 100 mM NH4Cl, 10 mM MgCl$_2$), and 6 mM β-mercaptoethanol. The 30S subunits were prepared in TNM buffer, placed at 42° C. for 2 min, then placed at room temperature. Aliquots of 30S subunits were added sequentially to the peptide at room temperature. A Varian Cary Eclipse Fluorescence Spectrophotometer was used with an excitation wavelength of 325 nm and emission maxima at 560 nm.

Example 2

Peptide Selection Method

The following example shows one way the selection method of the present invention can be used. In this example, a novel target site in a ribosomal unit was used to screen for peptides with affinity to the novel target site. In this example, the extended target molecule is an RNA/DNA hybrid construct wherein the DNA is tagged with biotin. Various other target molecules and affinity tags are contemplated in this invention as discussed above.

The affinity selection methodology was designed and developed using the two capture formats of magnetic beads and microtiter plates, and two elution systems including nonspecific elution, and specific elution by enzymatic digestion of the specifically designed poly-dA tail of H18 RNA with DNase I. H18 RNA at a concentration of 100 nM was allowed to interact with the phage library in solution in the presence of tRNA (2 μg/μL). The RNA-binding phage were captured using either capture format, and biotin was added to a final concentration of 0.1 mM in order to displace any streptavidin-binding phage from the solid support. Unbound phage were washed from the solid support with wash buffer supplemented with tween-20. The stringency of washes was increased for the magnetic beads capture system, by increasing the concentration of tween-20 from 0.1% to 0.5% after the first round of selection. The stringency of washes for the microtiter well plate system was kept constant throughout the rounds of selection by using a concentration of tween-20 of 0.05%. The bound phage were released from the solid support using an acidic buffer as a nonspecific eluant. After four rounds of selection the sequences of the phage-displayed peptides were obtained by sequencing of the phage DNA.

An additional round of selection was performed using the amplified eluate from the fourth round of magnetic beads selection. The bound phage were eluted by using DNase I. A separate affinity selection was carried out using the magnetic beads capture system and eluting the bound phage specifically with DNase I. Three rounds of selection were done. An overview of the selection process is shown in FIGS. 2A and B.

Twenty-six peptide motifs were obtained through the affinity selection process (Tables 1 and 2). After four rounds of selection using magnetic beads and nonspecific elution, 15 peptide sequences were obtained (Table 1), and the peptide motif AGAAMSH (BLS15) (SEQ ID NO. 2) was the most predominant. Three different peptide sequences were obtained from the fourth round of well plate capture selection (Table 1), and the peptide AMSAPIP (BLS18) (SEQ ID NO. 3) was the most predominant sequence. Interestingly, BLS15 and BLS18 obtained from magnetic beads and well plate selection respectively, contain a conserved three amino acid residue motif (AMS), which upon detailed structural analysis will give important information about the rules that govern peptide-RNA recognition, and will help in the development of new antibiotics targeting the new unexploited site H18 RNA.

Results from the magnetic beads selection with specific elution are shown in Table 2. After two rounds of selection seven peptide sequences were obtained, and the peptide sequence SILPYPY (SEQ ID NO. 4) (BLS26) was found to be the most predominant.

Alignment of the peptide sequences revealed the presence of several conserved motifs among the peptides. Some common motifs observed were AMS, HPP, THP, and LHL. Independently of the method of selection (magnetic beads or well plates), and elution (nonspecific or specific) conserved motifs were observed, such as peptides BLS18 (AMSAPIP) (SEQ ID NO. 3) and BLS2 (VQSLPSP) (SEQ ID NO.5) which were selected by well plates and magnetic beads respectively, and using nonspecific elution, sharing the common motif SXPXP (SEQ ID NO. 6) (X=any residue). Another motif selected was SXXLPT (SEQ ID NO. 7) from peptides BLS8 (LSPKLPT)

(SEQ ID NO. 8) and BLS23 (SSLLPTT) (SEQ ID NO. 9), selected by nonspecific elution and specific elution respectively, using magnetic beads. Common motifs can be used in combinatorial screening assays to find key residues within the motifs that are important for binding RNA, and this peptide scaffolds can also be used to build new drugs.

Peptide sequences obtained by the newly developed affinity selection methodology were synthesized to explore their ability as ribosomal inhibitors of protein synthesis, as well as to conduct more detailed studies of the interaction of the selected peptides with H18 RNA.

Example 3

The Indentified Peptides can Inhibit Protein Synthesis

Figure 3:
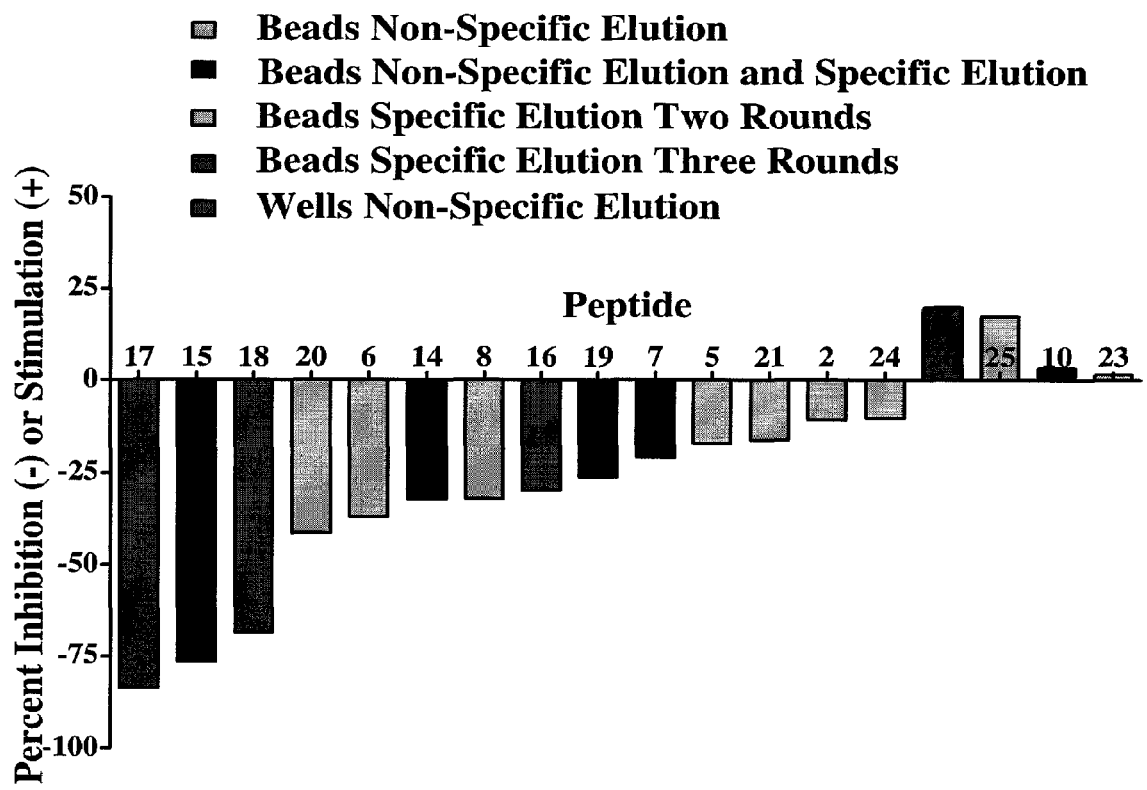
FIG. 3 is a bar graph comparing the peptides tested in the *E. coli* cell-free transcription-translation system for the inhibition or stimulation of synthesis of the firefly luciferase at 100 µM peptide concentration.
Figure 4A:
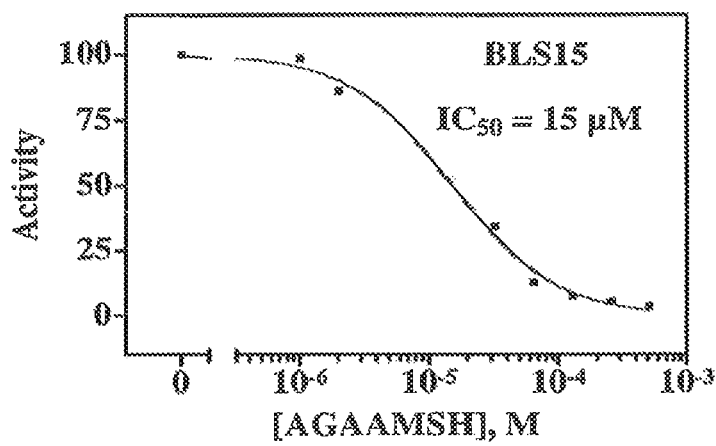
FIG. 4A is a graph showing the inhibition of firefly luciferase synthesis by BLS15 (SEQ ID NO. 2) in an *E. coli* cell-free transcription-translation system.
Figure 4B:
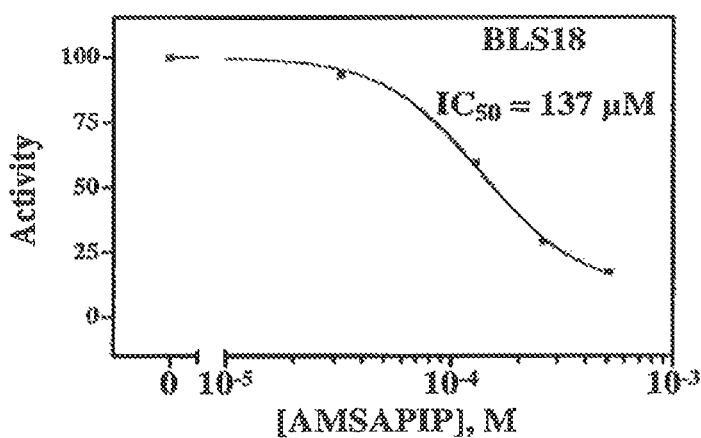
FIG. 4B is a graph showing the inhibition of firefly luciferase synthesis by BLS18 (SEQ ID NO. 3) in an *E. coli* cell-free transcription-translation system.
Figure 5A:
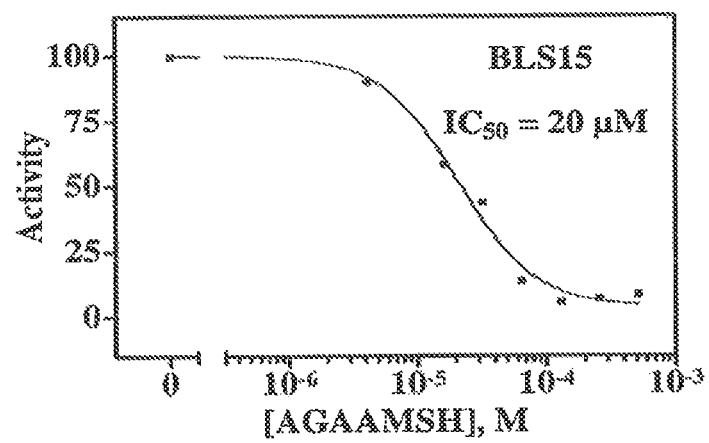
FIG. 5A is a graph showing the inhibition of firefly luciferase synthesis by BLS15 (SEQ ID NO. 2) in an eukaryotic cell-free translation system.
Figure 5B:
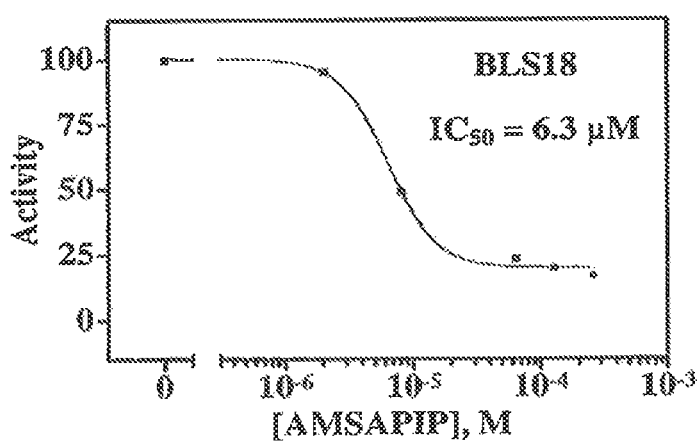
FIG. 5B is a graph showing the inhibition of firefly luciferase synthesis by BLS18 (SEQ ID NO. 3) in an eukaryotic cell-free translation system.

The synthesized peptides were tested for their inhibitory activity in protein synthesis using cell-free translation assays from E. coli. The system uses a circular DNA template in a coupled in vitro transcription/translation reaction for the production of the protein luciferase. The system was supplemented with the radiolabeled amino acid [$^{35}$S]methionine to measure total production of luciferase in the assay. Inhibition of luciferase synthesis by the selected peptides was tested at a peptide concentration of 100 µM. As was expected from the important functional role of H18-stem loop in the ribosomal subunit, inhibition of protein synthesis was observed. The strongest inhibitors of protein synthesis were peptides BLS15, BLS17, and BLS18 (FIG. 3) with a percent inhibition of 70-80%. Peptides BLS6, BLS14, and BLS20 inhibited protein synthesis by 30-40%. A 20% stimulation of protein synthesis was also observed by peptides BLS25 and BLS26. Strikingly, peptides BLS15 and BLS18 show high potency for inhibition of protein synthesis with and $IC_{50}$ of 15 µM and 137 µM (FIG. 4), respectively, and were the most common peptide found by magnetic bead and microtiter well capture selection. In addition, BLS15 was shown to inhibit synthesis of GFP in the coupled transcription-translation system. In accordance with the high conservation of H18 across the evolutionary domains, both peptides inhibited protein synthesis in the rabbit reticulocyte cell-free translation system with $IC_{50}$ of 20 µM (BLS15) and 6.3 µM (BLS18) (FIG. 5). Peptide BLS18 is a more potent inhibitor of protein synthesis in an eukaryotic system by 20-fold compared to a bacterial system, exhibiting its importance as a potential anticancer agent.

In an attempt to confirm the site of peptide binding, RNA footprinting was performed. No changes in RNA reactivity was observed in the presence of BLS15 or BLS18 with DMS, kethoxal, DEPC, or lead cleavage. Small changes in accessibility of 2'-hydroxyl of C522 and A523 to N-methylisatoic anhydride were observed in the presence of BLS15 as well as in the presence of streptomycin.

Example 4

Synergism Between Identified Peptides and Antibiotics

Combination drug therapy for treating infectious diseases can be used to counteract drug resistance. The activity of drugs in combination is crucial for treating bacteria that show resistance to any single antibiotic in clinical use, and is the last resource for treating patients until new antibiotics are discovered. The importance of combination therapies prompted us to test the selected peptides in combination with several antibiotics to investigate synergy in inhibition of protein synthesis in a bacterial system.

Figure 6:
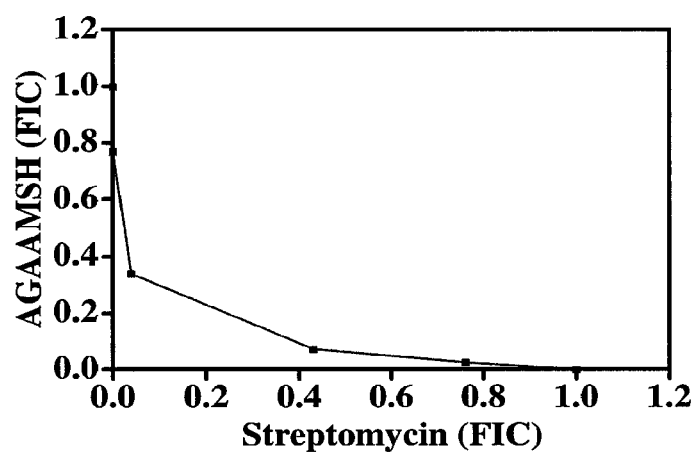
FIG. 6 is a graph showing the synergistic effect of BLS15 (SEQ ID NO. 2) with streptomycin.

BLS15 was tested in combination with streptomycin, an antibiotic that makes contacts with H18 and interferes with decoding, and showed synergistic action (FIG. 6). The potency of BLS15 in inhibiting protein synthesis in a bacterial system increased by 25-fold in the presence of 3 µM streptomycin. Other related antibiotics were tested, and a synergistic response was also observed. The newly identified peptides have a potential of being used in combination with other antibacterials to fight resistant bacteria, and they can be used as well by linking them to other antibiotics to enhance potency creating a new class of drugs; this technique will enhance the affinity and specificity of peptide-RNA ligands. A similar example to our technique is the linkage of two ribosomal antibiotics, sparsomycin and linezolid, creating a new compound that is active against a great variety of pathogens.

Example 5

Use of the Indentified Peptides in Screening Assays

A method to study the interactions of the identified peptides with H18 RNA was developed by tagging a fluorescent group to the peptide motif. Dansyl is a very sensitive fluorophore used to detect changes in the microenvironment of proteins, and was used as a reporter group to detect changes in the environment of identified peptides upon binding to the stem-loop H18 of 30S subunits. The advantage of this method is that modified peptides with a fluorophore are easy to synthesize, and it is a direct method of studying binding of peptides to ribosomes. The assay as defined by the present invention can be carried out with different detection methodology depending on the detectable tag or label which preferably may be selected from the list including, but not limited to, fluorescent labels, chemiluminescent labels, colorimetric labels, enzymatic markers, and radioactive isotopes. For example, the fluorescent label can be selected from the list consisting of dansyl, fluorescein, Oregon green, rhodamine, tetra-methyl rhodamine, Texas-red, phycoerythrin, BODIPY fluorophore, and $Eu^{3+}$.

The identified peptides can be used for screening of libraries of synthetic and natural organic compounds for drug leads affecting translation in bacterial and eukaryotic systems due to binding to H18 and impairment of its activity in protein synthesis. The peptides can be used in ligand-displacement assays, or as surrogate ligands for highthroughput screening of small-molecule libraries. Detailed structural information can be obtained from peptide-H18 complexes, such as thermodynamic and kinetic characterization, and will help in understanding ligand-RNA recognition and in the development of new class of RNA binders.

While the present invention has been described in terms of specific methods and compositions, it is understood that variations and modifications will occur to those skilled in the art upon consideration of the present invention. Those skilled in the art will appreciate, or be able to ascertain using no more than routine experimentation, further features and advantages of the invention based on the above-described embodiments. Accordingly, the invention is not to be limited by what has been particularly shown and described. All publications and references are herein expressly incorporated by reference in their entirety.

TABLE 1

| Phage clone | Peptide Sequence (SEQ ID NO:) | Found (%) |
|---|---|---|
| A. Magnetic Beads Capture Fourth Round (Nonspecific Elution) | | |
| BLS1 | FPGHSGP (10) | 2 |
| BLS2 | VQSLPSP (5) | 2 |
| BLS3 | EPLQLKM (11) | 2 |
| BLS4 | TPHNTST (12) | 2 |
| BLS5 | QWTWTQY (13) | 2 |
| BLS6 | LTHPRWP (14) | 2 |
| BLS7 | TKTDTWL (15) | 2 |
| BLS8 | LSPKLPT (8) | 2 |
| BLS9 | NTPQGMT (16) | 3 |
| BLS10 | THPLLLS (17) | 7 |
| BLS11 | GHWEARE (18) | 7 |
| BLS12 | AVPRASF (19) | 7 |
| BLS13 | YHPMPVP (20) | 8 |
| BLS14 | TPTTDGP (21) | 20 |
| BLS15 | AGAAMSH (2) | 32 |
| Fifth Round (DNase I Elution) | | |
| BLS19 | VHRHPPH (22) | 4 |
| BLS10 | THPLLLS (23) | 7 |
| BLS11 | GHWEARE (24) | 11 |
| BLS15 | AGAAMSH (2) | 21 |
| BLS7 | TKTDTWL (25) | 29 |
| BLS14 | TPTTDGP (26) | 29 |
| B. Microtiter Plates Capture Fourth Round (Nonspecific Elution) | | |
| BLS16 | MKHPPRI (27) | 2 |
| BLS17 | GTMLAAV (28) | 4 |
| BLS18 | AMSAPIP (3) | 94 |

TABLE 2

| Phage clone | Peptide Sequence (SEQ ID NO:) | Found (%) |
|---|---|---|
| Second Round (DNase I Elution) | | |
| BLS20 | TMTPPTR (29) | 6.6 |
| BLS21 | GNDWPHW (30) | 6.6 |
| BLS22 | EHPYITV (31) | 6.6 |
| BLS23 | SSLLPTT (9) | 6.6 |
| BLS24 | NTNTLHL (32) | 6.6 |
| BLS25 | SYPDLHL (33) | 6.6 |
| BLS26 | SILPYPY (4) | 60 |
| Third Round (DNase I Elution) | | |
| BLS26 | SILPYPY (4) | 100 |

The invention claimed is:

1. A method for treating a bacterial infection in a subject comprising administering a peptide that inhibits protein synthesis through an interaction at a stem-loop H18 in 16S rRNA of a 30S ribosomal subunit, wherein the peptide is the peptide of SEQ ID NO:28.

2. The method of claim 1, wherein the peptide is delivered in an amount sufficient to inhibit the growth of bacteria in vivo.

3. The method of claim 1, wherein said peptide is delivered locally or regionally to a site of infection.

4. The method of claim 1, wherein said peptide is administered to a wound site.

5. The method of claim 1, wherein said peptide is administered topically.

6. The method of claim 1, wherein said peptide is delivered systemically.

7. The method of claim 1, wherein said peptide is delivered via intravenous or intra-arterial injection.

8. The method of claim 1, further comprising administering to said subject one or more antimicrobial compounds.

9. A method for treating a microbial infection in a subject comprising administrating a peptide that inhibits protein synthesis through an interaction at a stem-loop H18 in 16S rRNA of a 30S ribosomal subunit in an amount sufficient to inhibit the growth of microbes in vivo, wherein the peptide is the peptide of SEQ ID NO:28.

10. A method for treating microbial growth in a solution comprising mixing said solution with a peptide that inhibits protein synthesis through an interaction at a stem-loop H18 in 16S rRNA of a 30S ribosomal subunit in an amount sufficient to inhibit the microbial growth in said solution, wherein the peptide is the peptide of SEQ ID NO:28.

* * * * *